(12) United States Patent (10) Patent No.: US 7,741,332 B2
McNaughton-Smith et al. (45) Date of Patent: *Jun. 22, 2010

(54) FUSED RING HETEROCYCLES AS POTASSIUM CHANNEL MODULATORS

(75) Inventors: Grant Andrew McNaughton-Smith, Morrisville, NC (US); George Salvatore Amato, Cary, NC (US); James Barnwell Thomas, Jr., Efland, NC (US)

(73) Assignee: Icagen, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/740,831

(22) Filed: Apr. 26, 2007

(65) Prior Publication Data

US 2008/0058319 A1 Mar. 6, 2008

Related U.S. Application Data

(63) Continuation of application No. 10/937,958, filed on Sep. 10, 2004, now Pat. No. 7,223,768.

(60) Provisional application No. 60/502,109, filed on Sep. 10, 2003.

(51) Int. Cl.
*A61K 31/517* (2006.01)
*C07D 239/72* (2006.01)
(52) U.S. Cl. .............................. 514/266.3; 514/266.31; 544/287; 544/289
(58) Field of Classification Search ................. 544/262, 544/287, 289; 514/262.1, 266.3, 266.31
See application file for complete search history.

(56) References Cited

U.S. PATENT DOCUMENTS 7,223,768 B2 * 5/2007 McNaughton-Smith et al. ....................... 514/266.3
2002/0128277 A1 9/2002 Dworetzky et al.

FOREIGN PATENT DOCUMENTS

WO WO01/92283 A2 12/2001

OTHER PUBLICATIONS

Abdel-Gawad et al., Bulletin of the Faculty of Pharmacy (Cairo Univ.) (1995), vol. 33, pp. 67-74.
Al-Sehemi et al., Chemical Communications (2001), vol. 24, pp. 2684-2685.
Archana et al., Indian Journal of Chemistry, Section B: Organic Chemistry Including Medicinal Chemistry (2002), 41B(11), pp. 2371-2373.
Bajaj et al., Arzneitmittel-Forschung (2003), 53(7), pp. 480-485.
Buu-Hoi, N.P., et al. "Synthesis and pharmacological properties of urethane and urea derivatives of heterocyclic amines", *Chemical Abstract* (1966) vol. 65, Abstract #12305 (CAPLUS Accession No. 1966:412305).
Desai, N.C., et al. "Synthesis of substituted quinazolone derivatives as potential anti-HIV agents", Part III., *Chemical Abstract*, (1996) vol. 125, Abstract #75356 (CAPLUS Accession No. 1996:377710).
El-Helby et al., Al-Azhar Journal of Pharmaceutical Sciences (2001), vol. 28, pp. 73-88.
Klosa, J. "Synthesis of amides in the quinazolone series.", *Chemical Abstract* (1966) vol. 65, Abstract #12304 (CAPLUS Accession No. 1966:412304).
Mohamed, M.M., "Reactions of 3-amino-2-propyl-4(3H)-quinazolinone with aromatic aldehydes, nitrogen nucleophiles, and esters", *Chemical Abstract* (1983) vol. 99, Abstract #38433 (CAPLUS Accession No. 1983:438433).
Smith, K., et al. "Lithiation of 3-(Acylamino)-2-unsubstituted-, 3-(Acylamino)-2-ethyl-, and 3-(Acylamino)-2-propyl-4(3*H*)-quinazolinones: Convenient Synthesis of More Complex Quinazolinones", *J. Org. Chem.* (1996) 61:647-655.
Srivastava et al., Asian Journal of Chemistry (2000), vol. 12, pp. 243-246.
Varnavas, A., et al. "Quinazolinone derivatives: synthesis and binding evaluation on cholecystokinin receptors", *Chemical Abstract* (1996), vol. 125, Abstract #75354 (CAPLUS Accession No. 1996:377707).
Alonso, G. et al. "Synthesis of condensed heterocyclic systems of pyrazole," DATABASE CA [Online] Chemical Abstracts Service, Columbus, Ohio, US; XP002519397; retrieved from STN Database accession No. 1977:567969 abstract and Anales De Quimica (1968-1979) 72(11-12): 897-901 CODEN: ANQUBU; ISSN: 0365-4990 (1976).
Ossman, Abdel Rahman El Nasser et al, "Synthesis and pharmacological activity of some new 4(3H)-quinazolone derivatives," DATABASE CA [Online] Chemical Abstracts Service, Columbus, Ohio, US; XP002519399, retrieved from STN Database accession No. 1985:596047 abstract and Indian Journal of Chemistry, Section B: Organic Chemistry including Medicinal Chemistry, 248(3), 335-5 CODEN: IJSBDB; ISSN: 0376-4699 (1985).

(Continued)

*Primary Examiner*—Rei-tsang Shiao
(74) *Attorney, Agent, or Firm*—Townsend and Townsend and Crew LLP

(57) ABSTRACT

Compounds, compositions and methods are provided which are useful in the treatment of diseases through the modulation of potassium ion flux through voltage-dependent potassium channels. More particularly, the invention provides quinazolinone, compositions and methods that are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety and motor neuron diseases, maintaining bladder control or treating urinary incontinence) and as neuroprotective agents (e.g., to prevent stroke and the like) by modulating potassium channels associated with the onset or recurrence of the indicated conditions.

45 Claims, 13 Drawing Sheets

OTHER PUBLICATIONS

Ibrahim, Salah S. et al., "Synthesis and biological evaluation of some new fusd quinazoline derivatives," DATABASE CA [Online] Chemical Abstracts Service, Columbus, Ohio, US; XP002519402, retrieved from STN Database accession No. 1997:481782 abstract and Journal of Chemical Research, Synopses 5:154-155, CODEN: JRPSDC; ISSN: 0308-2342 (1997).

* cited by examiner

| ID# | MOLSTRUCTURE | ID# | MOLSTRUCTURE | ID# | MOLSTRUCTURE |
|---|---|---|---|---|---|
| 1 |  | 13 |  | 25 |  |
| 2 |  | 14 |  | 26 |  |
| 3 |  | 15 |  | 27 |  |
| 4 |  | 16 |  | 28 |  |
| 5 |  | 17 |  | 29 |  |
| 6 |  | 18 |  | 30 |  |
| 7 |  | 19 |  | 31 |  |
| 8 |  | 20 |  | 32 |  |
| 9 |  | 21 |  | 33 |  |
| 10 |  | 22 |  | 34 |  |
| 11 |  | 23 |  | 35 |  |
| 12 |  | 24 |  | 36 |  |

| ID# | MOLSTRUCTURE | ID# | MOLSTRUCTURE | ID# | MOLSTRUCTURE |
|---|---|---|---|---|---|
| 37 |  | 50 |  | 63 |  |
| 38 |  | 51 |  | 64 |  |
| 39 |  | 52 |  | 65 |  |
| 40 |  | 53 |  | 66 |  |
| 41 |  | 54 |  | 67 |  |
| 42 |  | 55 |  | 68 |  |
| 43 |  | 56 |  | 69 |  |
| 44 |  | 57 |  | 70 |  |
| 45 |  | 58 |  | 71 |  |
| 46 |  | 59 |  | 72 |  |
| 47 |  | 60 |  | 73 |  |
| 48 |  | 61 |  | 74 |  |
| 49 |  | 62 |  | 75 |  |

| ID# | MOLSTRUCTURE | ID# | MOLSTRUCTURE | ID# | MOLSTRUCTURE |
|---|---|---|---|---|---|
| 76 |  | 89 |  | 102 |  |
| 77 |  | 90 |  | 103 |  |
| 78 |  | 91 |  | 104 |  |
| 79 |  | 92 |  | 105 |  |
| 80 |  | 93 |  | 106 |  |
| 81 |  | 94 |  | 107 |  |
| 82 |  | 95 |  | 108 |  |
| 83 |  | 96 |  | 109 |  |
| 84 |  | 97 |  | 110 |  |
| 85 |  | 98 |  | 111 |  |
| 86 |  | 99 |  | 112 |  |
| 87 |  | 100 |  | 113 |  |
| 88 |  | 101 |  | 114 |  |

| ID# | MOLSTRUCTURE | ID# | MOLSTRUCTURE | ID# | MOLSTRUCTURE |
|---|---|---|---|---|---|
| 115 |  | 128 |  | 141 |  |
| 116 |  | 129 |  | 142 |  |
| 117 |  | 130 |  | 143 |  |
| 118 |  | 131 |  | 144 |  |
| 119 |  | 132 |  | 145 |  |
| 120 |  | 133 |  | 146 |  |
| 121 |  | 134 |  | 147 |  |
| 122 |  | 135 |  | 148 |  |
| 123 |  | 136 |  | 149 |  |
| 124 |  | 137 |  | 150 |  |
| 125 |  | 138 |  | 151 |  |
| 126 |  | 139 |  | 152 |  |
| 127 |  | 140 |  | 153 |  |

5/13

| ID# | MOLSTRUCTURE | ID# | MOLSTRUCTURE | ID# | MOLSTRUCTURE |
|---|---|---|---|---|---|
| 154 |  | 167 |  | 180 |  |
| 155 |  | 168 |  | 181 |  |
| 156 |  | 169 |  | 182 |  |
| 157 |  | 170 |  | 183 |  |
| 158 |  | 171 |  | 184 |  |
| 159 |  | 172 |  | 185 |  |
| 160 |  | 173 |  | 186 |  |
| 161 |  | 174 |  | 187 |  |
| 162 |  | 175 |  | 188 |  |
| 163 |  | 176 |  | 189 |  |
| 164 |  | 177 |  | 190 |  |
| 165 |  | 178 |  | 191 |  |
| 166 |  | 179 |  | 192 |  |

Fig. 1
6/13

| ID# | MOLSTRUCTURE | ID# | MOLSTRUCTURE | ID# | MOLSTRUCTURE |
|-----|--------------|-----|--------------|-----|--------------|
| 232 |  | 245 |  | 257 |  |
| 233 |  | 246 |  | 258 |  |
| 234 |  | 247 |  | 259 |  |
| 235 |  | 248 |  | 260 |  |
| 236 |  | 249 |  | 261 |  |
| 237 |  | 250 |  | 262 |  |
| 238 |  | 251 |  | 263 |  |
| 239 |  | 252 |  | 264 |  |
| 240 |  | 253 |  | 265 |  |
| 241 |  | 254 |  | 266 |  |
| 242 |  | 255 |  | 267 |  |
| 243 |  | 256 |  | 268 |  |
| 244 |  | 257 |  | 269 |  |

| ID# | MOLSTRUCTURE | ID# | MOLSTRUCTURE | ID# | MOLSTRUCTURE |
|-----|---|-----|---|-----|---|
| 348 |  | 361 |  | 374 |  |
| 349 |  | 362 |  | 375 |  |
| 350 |  | 363 |  | 376 |  |
| 351 |  | 364 |  | 377 |  |
| 352 |  | 365 |  | 378 |  |
| 353 |  | 366 |  | 379 |  |
| 354 |  | 367 |  | 380 |  |
| 355 |  | 368 |  | 381 |  |
| 356 |  | 369 |  | 382 |  |
| 357 |  | 370 |  | 383 |  |
| 358 |  | 371 |  | 384 |  |
| 359 |  | 372 |  | 385 |  |
| 360 |  | 373 |  | 386 |  |

Fig. 1

| ID# | MOLSTRUCTURE | ID# | MOLSTRUCTURE | ID# | MOLSTRUCTURE |
|---|---|---|---|---|---|
| 426 |  | 439 |  | 452 |  |
| 427 |  | 440 |  | 453 |  |
| 428 |  | 441 |  | 454 |  |
| 429 |  | 442 |  | 455 |  |
| 430 |  | 443 |  | 456 |  |
| 431 |  | 444 |  | 457 |  |
| 432 |  | 445 |  | 458 |  |
| 433 |  | 446 |  | 459 |  |
| 434 |  | 447 |  | 460 |  |
| 435 |  | 448 |  | 461 |  |
| 436 |  | 449 |  | 462 |  |
| 437 |  | 450 |  | 463 |  |
| 438 |  | 451 |  | 464 |  |

Fig. 1

| ID# | MOLSTRUCTURE | ID# | MOLSTRUCTURE | ID# | MOLSTRUCTURE |
|---|---|---|---|---|---|
| 465 | | 478 | | | |
| 466 | | 479 | | | |
| 467 | | 480 | | | |
| 468 | | 481 | | | |
| 469 | | 482 | | | |
| 470 | | 483 | | | |
| 471 | | 484 | | | |
| 472 | | 485 | | | |
| 473 | | 486 | | | |
| 474 | | 487 | | | |
| 475 | | 488 | | | |
| 476 | | 489 | | | |
| 477 | | 490 | | | |

FUSED RING HETEROCYCLES AS POTASSIUM CHANNEL MODULATORS

FIELD OF THE INVENTION

This invention relates to the use of certain fused ring heterocycles as potassium channel modulators and to the treatment of diseases in which a potassium channel is implicated. Additionally, this invention relates to novel compounds that are useful as potassium channel modulators.

BACKGROUND OF THE INVENTION

Ion channels are cellular proteins that regulate the flow of ions, including calcium, potassium, sodium and chloride, into and out of cells. These channels are present in all human cells and affect such processes as nerve transmission, muscle contraction and cellular secretion. Among the ion channels, potassium channels are the most ubiquitous and diverse, being found in a variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels are associated with a number of physiological processes, including regulation of heartbeat, dilation of arteries, release of insulin, excitability of nerve cells, and regulation of renal electrolyte transport. Potassium channels are made by alpha subunits that fall into at least 8 families, based on predicted structural and functional similarities (Wei et al., *Neuropharmacology* 35(7): 805-829 (1997)). Three of these families (Kv, eag-related, and KQT) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels, or BK channels have seven transmembrane domains (Meera et al., *Proc. Natl. Acad. Sci. U.S.A.* 94(25): 14066-71 (1997)) and are gated by both voltage and calcium or pH (Schreiber et al., *J. Biol. Chem.* 273: 3509-16 (1998)). Another family, the inward rectifier potassium channels (Kir), belongs to a structural family containing two transmembrane domains, and an eighth functionally diverse family (TP, or "two-pore") contains two tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels made from Kv, KQT and Slo or BK subunits have often been found to contain additional, structurally distinct auxiliary, or beta, subunits. These subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493: 625-633 (1996); Shi et al., *Neuron* 16(4): 843-852 (1996)). In another example, the KQT family beta subunit, minK, primarily changes activation kinetics (Sanguinetti et al., *Nature* 384: 80-83 (1996)).

Slo or BK potassium channels are large conductance potassium channels found in a wide variety of tissues, both in the central nervous system and periphery. They play a key role in the regulation of processes such as neuronal integration, muscular contraction and hormone secretion. They may also be involved in processes such as lymphocyte differentiation and cell proliferation, spermatocyte differentiation and sperm motility. Three alpha subunits of the Slo family have been cloned, i.e., Slo1, Slo2, and Slo3 (Butler et al., *Science* 261: 221-224 (1993); Schreiber et al., *J. Biol. Chem.*, 273: 3509-16 (1998); and Joiner et al., *Nature Neurosci.* 1: 462-469 (1998)). These Slo family members have been shown to be voltage and/or calcium gated, and/or regulated by intracellular pH.

Certain members of the Kv family of potassium channels were recently renamed (see, Biervert, et al., *Science* 279: 403-406 (1998)). KvLQT1 was re-named KCNQ1, and the KvLQT1-related channels (KvLR1 and KvLR2) were renamed KCNQ2 and KCNQ3, respectively. More recently, additional members of the KCNQ subfamily were identified. For example, KCNQ4 was identified as a channel expressed in sensory outer hair cells (Kubisch, et al., *Cell* 96(3): 437-446 (1999)). KCNQ5 (Kananura et al., *Neuroreport* 11(9): 2063 (2000)), KCNQ 2/3 (Main et al., *Mol. Pharmacol.* 58: 253-62 (2000), KCNQ 3/5 (Wickenden et al., *Br. J. Pharma* 132: 381 (2001)) and KCNQ6 have also recently been described.

KCNQ2 and KCNQ3 have been shown to be nervous system-specific potassium channels associated with benign familial neonatal convulsions ("BFNC"), a class of idiopathic generalized epilepsy (see, Leppert, et al., *Nature* 337: 647-648 (1989)). These channels have been linked to M-current channels (see, Wang, et al., *Science* 282: 1890-1893 (1998)). The discovery and characterization of these channels and currents provides useful insights into how these voltage dependent (Kv) potassium channels function in different environments, and how they respond to various activation mechanisms. Such information has now led to the identification of modulators of KCNQ2 and KCNQ3 potassium channels or the M-current, and the use of such modulators as therapeutic agents. The modulators are the subject of the present invention.

SUMMARY OF THE INVENTION

The present invention provides fused ring heterocycles and pharmaceutically acceptable salts thereof ("compounds of the invention"), which are useful in the treatment of diseases through the modulation of potassium ion flux through voltage-dependent potassium channels.

In one aspect, the present invention provides compounds of the formula:

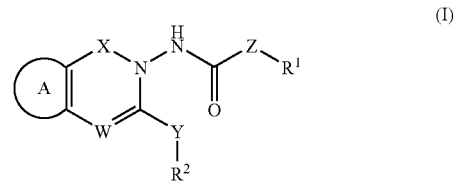

(I)

in which the symbol A represents a ring system such as a five- or six-membered substituted or unsubstituted aryl, a five- and six-membered substituted or unsubstituted heteroaryl, a substituted or unsubstituted $C_4$-$C_8$ cycloalkyl, or a substituted or unsubstituted 5-8 membered heterocyclyl.

In an exemplary embodiment, A is substituted or unsubstituted phenyl. Exemplary substituted phenyl moieties include those that are substituted with one or two groups that are independently selected from halogen, nitrile, substituted or unsubstituted $C_1$-$C_4$ alkyl, $SCF_3$, trifluoromethyl and trifluoromethoxy.

X is a moiety such as CO, CS or $SO_2$. The symbol W represents N or $CR^3$, in which $R^3$ is H, F, substituted or unsubstituted aryl, substituted or unsubstituted heteroaryl, substituted or unsubstituted $C_3$-$C_8$ cycloalkyl, substituted or unsubstituted 5-7 membered heterocyclyl, or substituted or unsubstituted $C_1$-$C_8$ alkyl.

The symbol Z indicates a bond, —$CH_2$—, —CHF—, —$CF_2$—, —CH=CH— or —$NR^4(CR^{4a}R^{4b})_s$—, wherein $R^4$ is a member selected from H and a substituted or unsubstituted $C_1$-$C_5$ alkyl group. The symbols $R^{4a}$ and $R^{4b}$ represent groups that are independently selected from H, substituted or unsubstituted aryl, substituted or unsubstituted heteroaryl, substituted or unsubstituted $C_3$-$C_8$ cycloalkyl, substituted or unsubstituted 5-7 membered heterocyclyl, or substituted or unsubstituted $C_1$-$C_8$ alkyl. The symbol s represents an integer from 1 to 3; Y represents $(CR^5R^6)_n$, in which n is an integer from 0-4. In a preferred embodiment, when n is 0 and $R^2$ is methyl, A is not an unsubstituted phenyl moiety.

$R^5$ and $R^6$ independently represent H, substituted or unsubstituted aryl, substituted or unsubstituted heteroaryl, substituted or unsubstituted $C_3$-$C_8$ cycloalkyl, substituted or unsubstituted 5-7 membered heterocyclyl, or substituted or unsubstituted $C_1$-$C_8$ alkyl.

The symbol $R^1$ represents a moiety that is selected from substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl.

In an exemplary embodiment, $R^1$ is substituted or unsubstituted phenyl. When $R^1$ is substituted phenyl, it is preferably substituted by one or more independently selected moiety, such as halogen, $CF_3$ or $OCF_3$.

$R^2$ is $CF_3$, substituted or unsubstituted $C_1$-$C_8$ alkyl, substituted or unsubstituted aryl, substituted or unsubstituted heteroaryl, substituted or unsubstituted $C_3$-$C_8$ cycloalkyl, substituted or unsubstituted 3-7-membered heterocyclyl. $R^2$ is preferably a substituted or unsubstituted $C_1$-$C_6$ saturated acyclic alkyl group, more preferably a $C_1$-$C_4$ saturated acyclic alkyl group.

In another aspect, the present invention provides pharmaceutical compositions comprising a pharmaceutically acceptable excipient and a compound of the formula provided above.

In yet another aspect, the present invention provides a method for increasing flow through voltage dependent potassium channels in a cell, comprising contacting the cell with a compound of the formula provided above in an amount sufficient to open the potassium channels.

In still another aspect, the present invention provides a method for treating a central or peripheral nervous system disorder or condition through the modulation of a voltage-dependent potassium channel, the method comprising administering to a subject in need of such treatment an effective amount of a compound of the formula provided above.

Other objects and advantages of the present invention will be apparent from the detailed description that follows.

DETAILED DESCRIPTION OF THE INVENTION AND THE PREFERRED EMBODIMENTS

Figure 1:
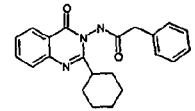
FIG. 1 displays structures of representative compounds of the invention.
Figure 1:
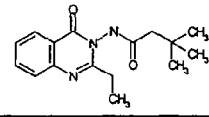
Figure 1:
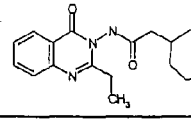
Figure 1:
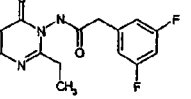
Figure 1:
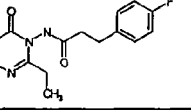
Figure 1:
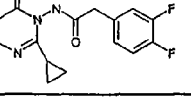
Figure 1:
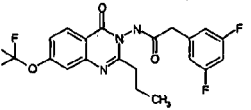
Figure 1:
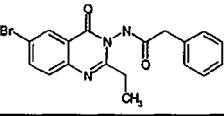
Figure 1:
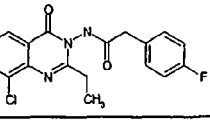
Figure 1:
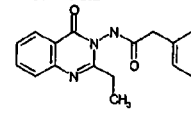
Figure 1:
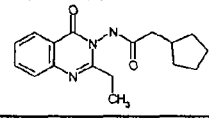
Figure 1:
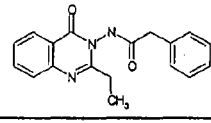
Figure 1:
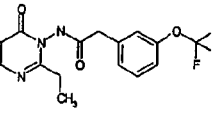
Figure 1:
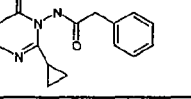
Figure 1:
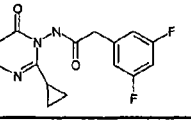
Figure 1:
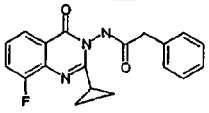
Figure 1:
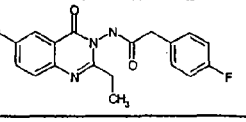
Figure 1:
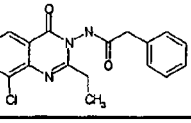
Figure 1:
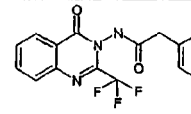
Figure 1:
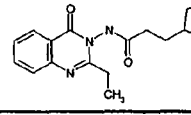
Figure 1:
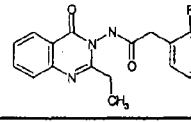
Figure 1:
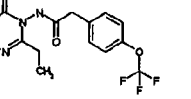
Figure 1:
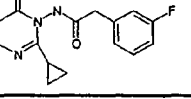
Figure 1:
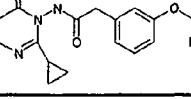
Figure 1:
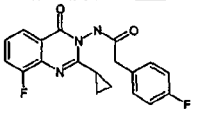
Figure 1:
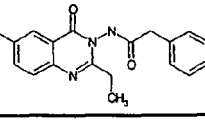
Figure 1:
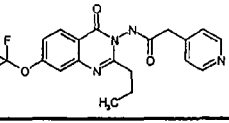
Figure 1:
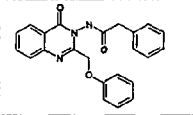
Figure 1:
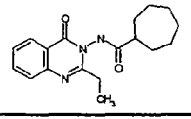
Figure 1:
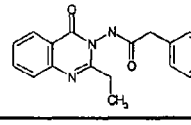
Figure 1:
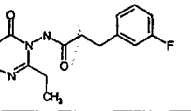
Figure 1:
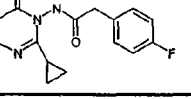
Figure 1:
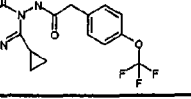
Figure 1:
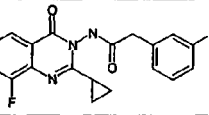
Figure 1:
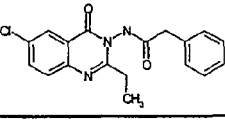
Figure 1:
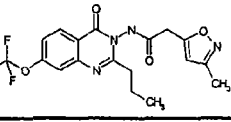
Figure 1:
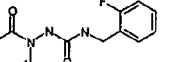
Figure 1:
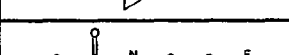
Figure 1:
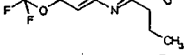
Figure 1:
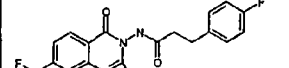
Figure 1:
Figure 1:
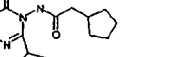
Figure 1:
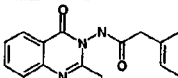
Figure 1:
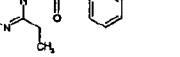
Figure 1:
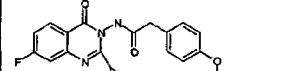
Figure 1:
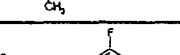
Figure 1:
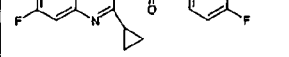
Figure 1:
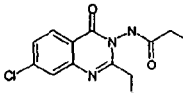
Figure 1:
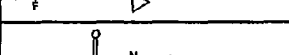
Figure 1:
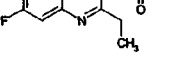
Figure 1:
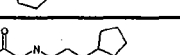
Figure 1:
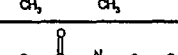
Figure 1:
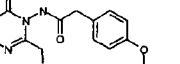
Figure 1:
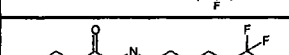
Figure 1:
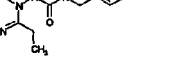
Figure 1:
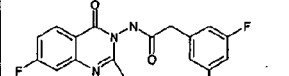
Figure 1:
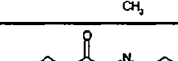
Figure 1:
Figure 1:
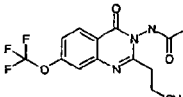
Figure 1:
Figure 1:
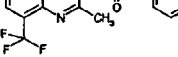
Figure 1:
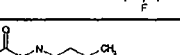
Figure 1:
Figure 1:
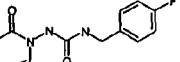
Figure 1:
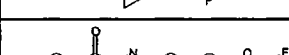
Figure 1:
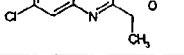
Figure 1:
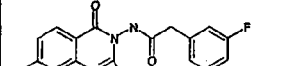
Figure 1:
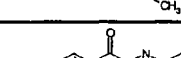
Figure 1:
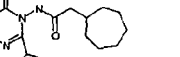
Figure 1:
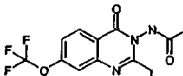
Figure 1:
Figure 1:
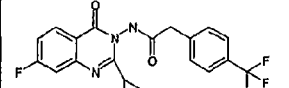
Figure 1:
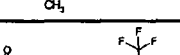
Figure 1:
Figure 1:
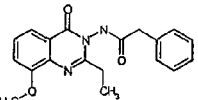
Figure 1:
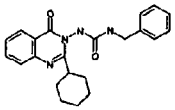
Figure 1:
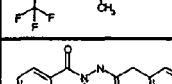
Figure 1:
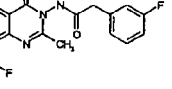
Figure 1:
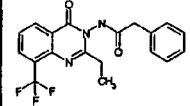
Figure 1:
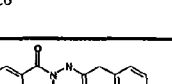
Figure 1:
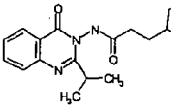
Figure 1:
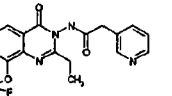
Figure 1:
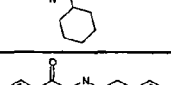
Figure 1:
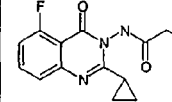
Figure 1:
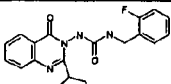
Figure 1:
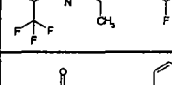
Figure 1:
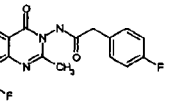
Figure 1:
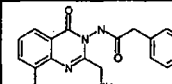
Figure 1:
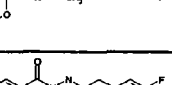
Figure 1:
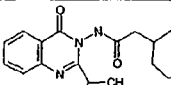
Figure 1:
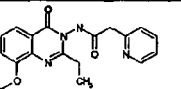
Figure 1:
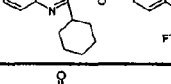
Figure 1:
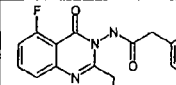
Figure 1:
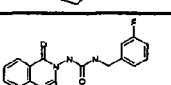
Figure 1:
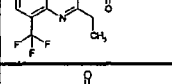
Figure 1:
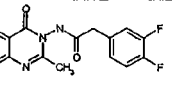
Figure 1:
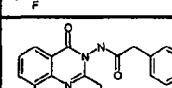
Figure 1:
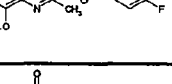
Figure 1:
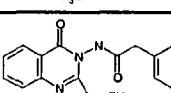
Figure 1:
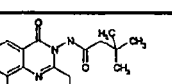
Figure 1:
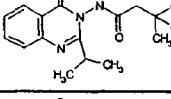
Figure 1:
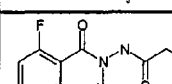
Figure 1:
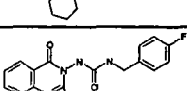
Figure 1:
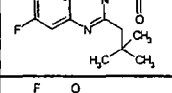
Figure 1:
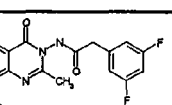
Figure 1:
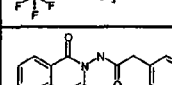
Figure 1:
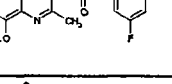
Figure 1:
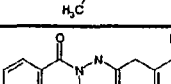
Figure 1:
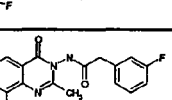
Figure 1:
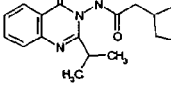
Figure 1:
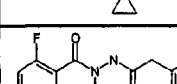
Figure 1:
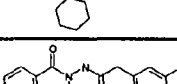
Figure 1:
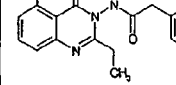
Figure 1:
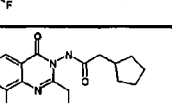
Figure 1:
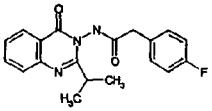
Figure 1:
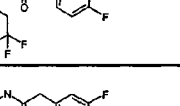
Figure 1:
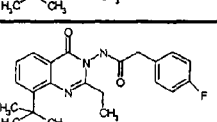
Figure 1:
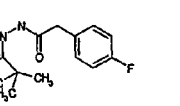
Figure 1:
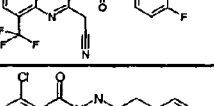
Figure 1:
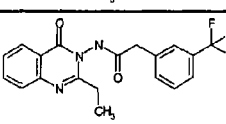
Figure 1:
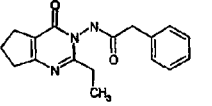
Figure 1:
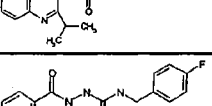
Figure 1:
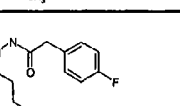
Figure 1:
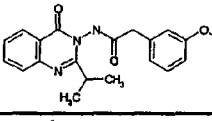
Figure 1:
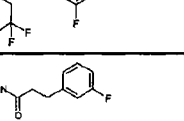
Figure 1:
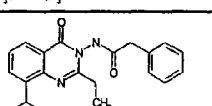
Figure 1:
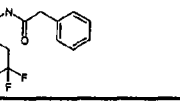
Figure 1:
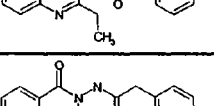
Figure 1:
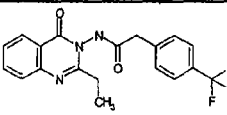
Figure 1:
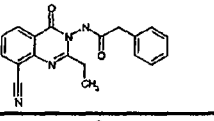
Figure 1:
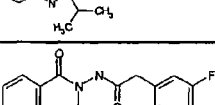
Figure 1:
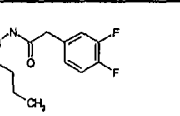
Figure 1:
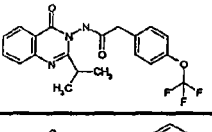
Figure 1:
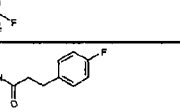
Figure 1:
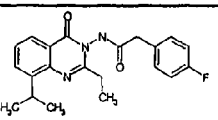
Figure 1:
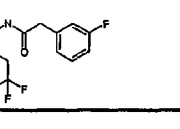
Figure 1:
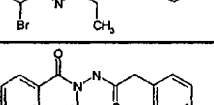
Figure 1:
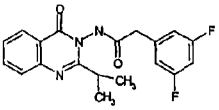
Figure 1:
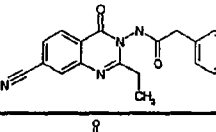
Figure 1:
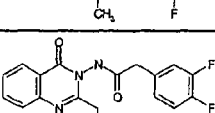
Figure 1:
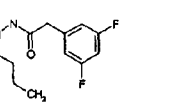
Figure 1:
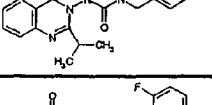
Figure 1:
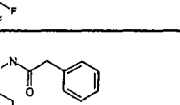
Figure 1:
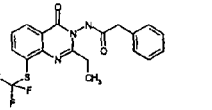
Figure 1:
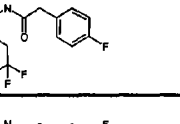
Figure 1:
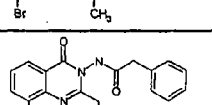
Figure 1:
Figure 1:
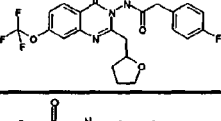
Figure 1:
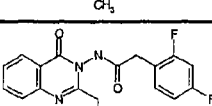
Figure 1:
Figure 1:
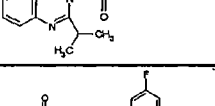
Figure 1:
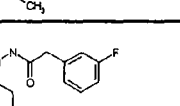
Figure 1:
Figure 1:
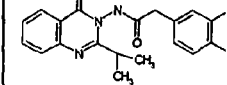
Figure 1:
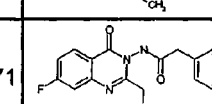
Figure 1:
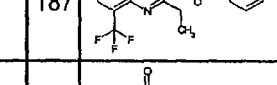
Figure 1:
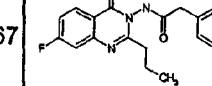
Figure 1:
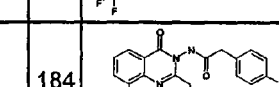
Figure 1:
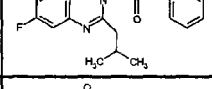
Figure 1:
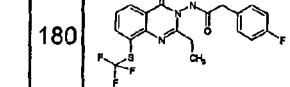
Figure 1:
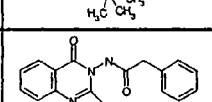
Figure 1:
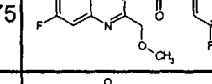
Figure 1:
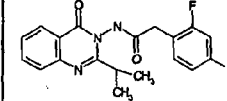
Figure 1:
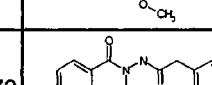
Figure 1:
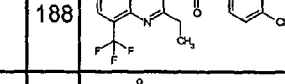
Figure 1:
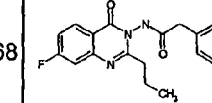
Figure 1:
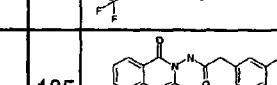
Figure 1:
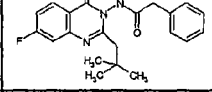
Figure 1:
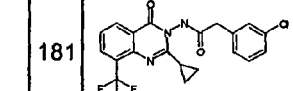
Figure 1:
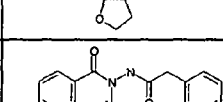
Figure 1:
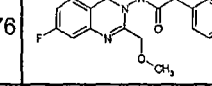
Figure 1:
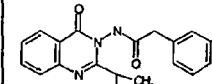
Figure 1:
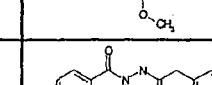
Figure 1:
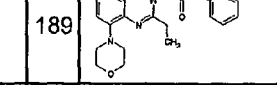
Figure 1:
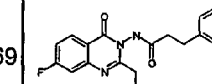
Figure 1:
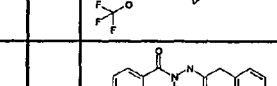
Figure 1:
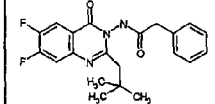
Figure 1:
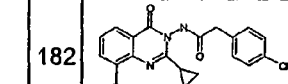
Figure 1:
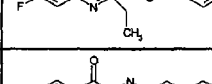
Figure 1:
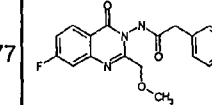
Figure 1:
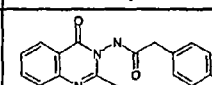
Figure 1:
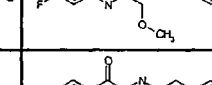
Figure 1:
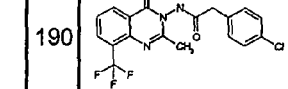
Figure 1:
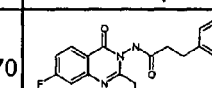
Figure 1:
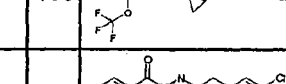
Figure 1:
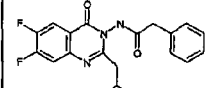
Figure 1:
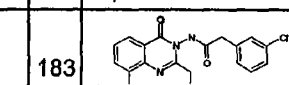
Figure 1:
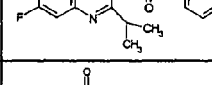
Figure 1:
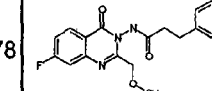
Figure 1:
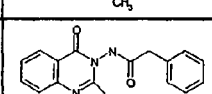
Figure 1:
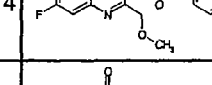
Figure 1:
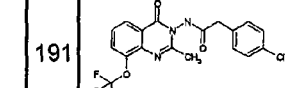
Figure 1:
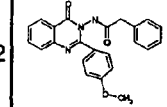
Figure 1:
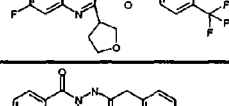
Figure 1:
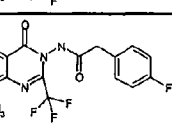
Figure 1:
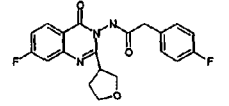
Figure 1:
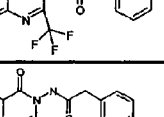
Figure 1:
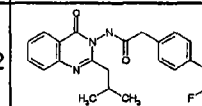
Figure 1:
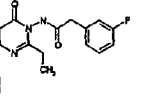
Figure 1:
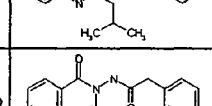
Figure 1:
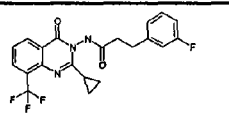
Figure 1:
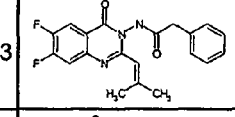
Figure 1:
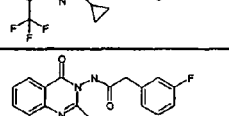
Figure 1:
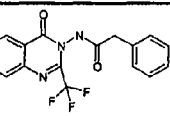
Figure 1:
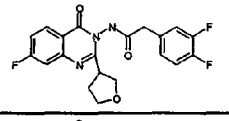
Figure 1:
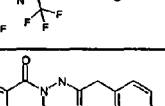
Figure 1:
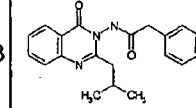
Figure 1:
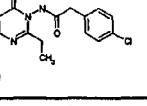
Figure 1:
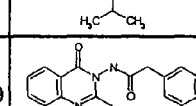
Figure 1:
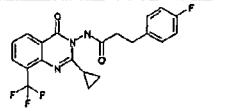
Figure 1:
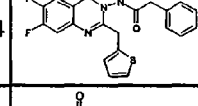
Figure 1:
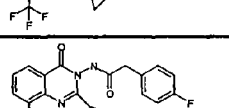
Figure 1:
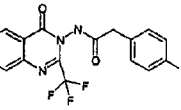
Figure 1:
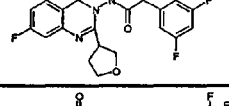
Figure 1:
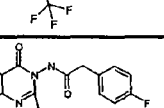
Figure 1:
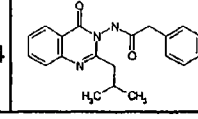
Figure 1:
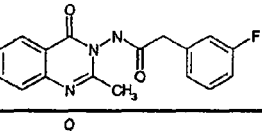
Figure 1:
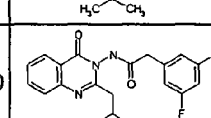
Figure 1:
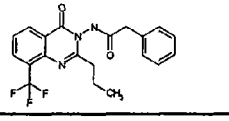
Figure 1:
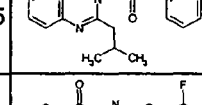
Figure 1:
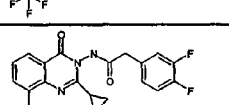
Figure 1:
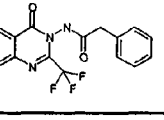
Figure 1:
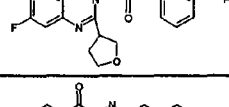
Figure 1:
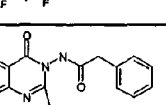
Figure 1:
Figure 1:
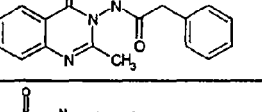
Figure 1:
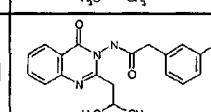
Figure 1:
Figure 1:
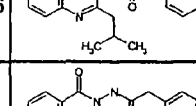
Figure 1:
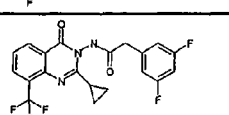
Figure 1:
Figure 1:
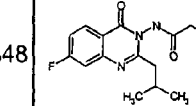
Figure 1:
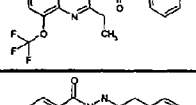
Figure 1:
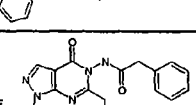
Figure 1:
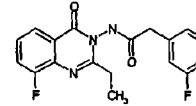
Figure 1:
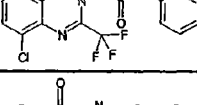
Figure 1:
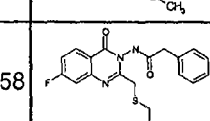
Figure 1:
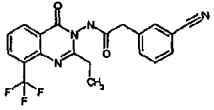
Figure 1:
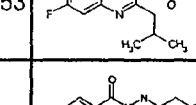
Figure 1:
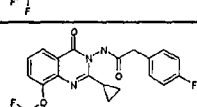
Figure 1:
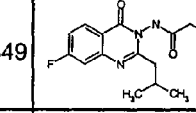
Figure 1:
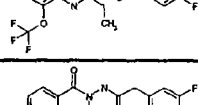
Figure 1:
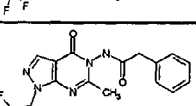
Figure 1:
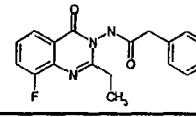
Figure 1:
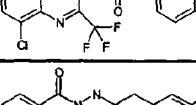
Figure 1:
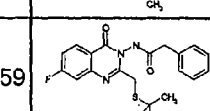
Figure 1:
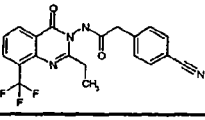
Figure 1:
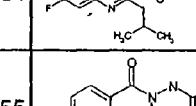
Figure 1:
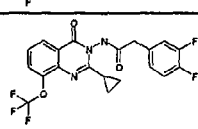
Figure 1:
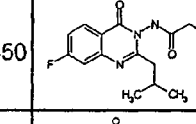
Figure 1:
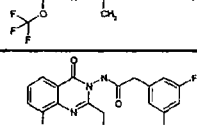
Figure 1:
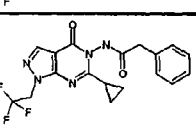
Figure 1:
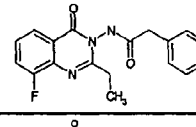
Figure 1:
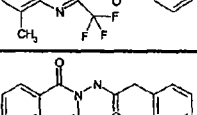
Figure 1:
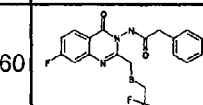
Figure 1:
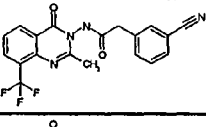
Figure 1:
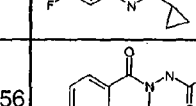
Figure 1:
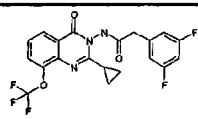
Figure 1:
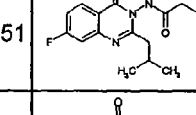
Figure 1:
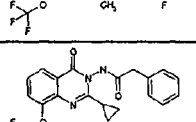
Figure 1:
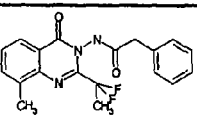
Figure 1:
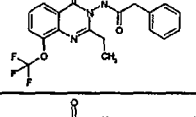
Figure 1:
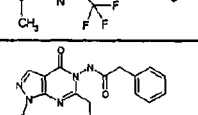
Figure 1:
Figure 1:
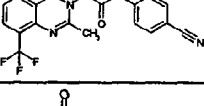
Figure 1:
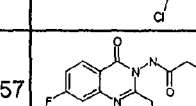
Figure 1:
Figure 1:
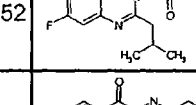
Figure 1:
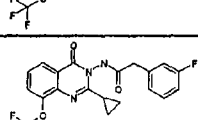
Figure 1:
Figure 1:
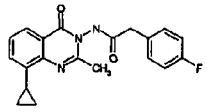
Figure 1:
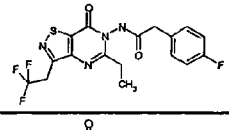
Figure 1:
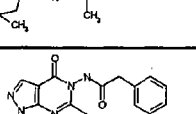
Figure 1:
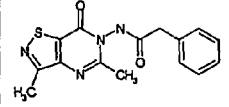
Figure 1:
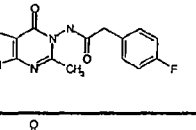
Figure 1:
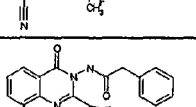
Figure 1:
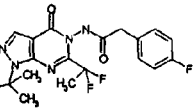
Figure 1:
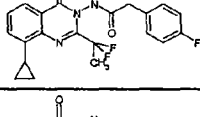
Figure 1:
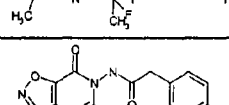
Figure 1:
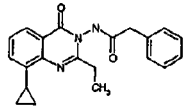
Figure 1:
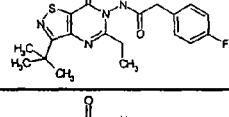
Figure 1:
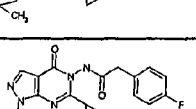
Figure 1:
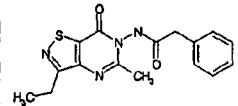
Figure 1:
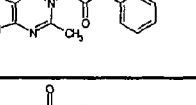
Figure 1:
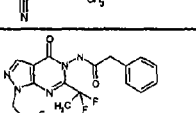
Figure 1:
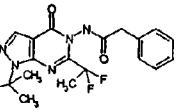
Figure 1:
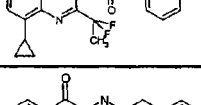
Figure 1:
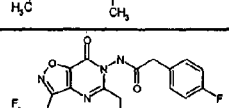
Figure 1:
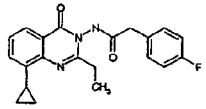
Figure 1:
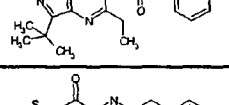
Figure 1:
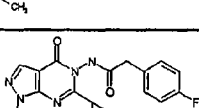
Figure 1:
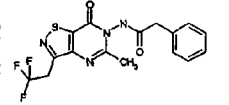
Figure 1:
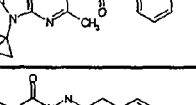
Figure 1:
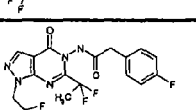
Figure 1:
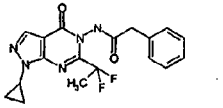
Figure 1:
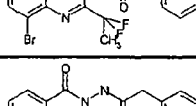
Figure 1:
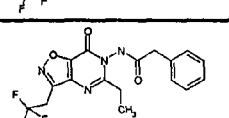
Figure 1:
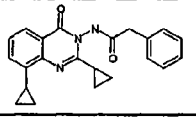
Figure 1:
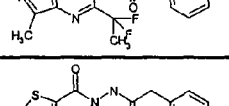
Figure 1:
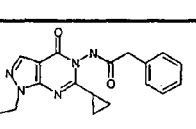
Figure 1:
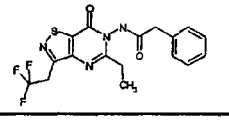
Figure 1:
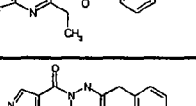
Figure 1:
Figure 1:
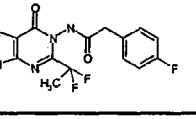
Figure 1:
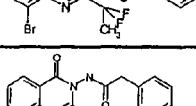
Figure 1:
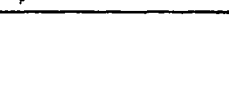
Figure 1:
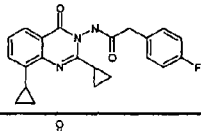
Figure 1:
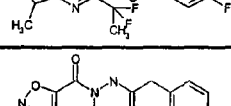
Figure 1:

Abbreviations and Definitions:

The abbreviations used herein have their conventional meaning within the chemical and biological arts. For example: CHO, Chinese hamster ovary; EBSS, Earl's Balanced Salt Solution; KCNQ, potassium channel Q; KCNQ2, potassium channel Q2, hSK, $Ca^{2+}$ activated small conductance potassium channels; SDS, sodium dodecyl sulfate; $Et_3N$, triethylamine; MeOH, methanol; and DMSO, dimethylsulfoxide.

"Compound of the invention," as used herein refers to a compound according to Formulae (I)-(V) or a combination thereof, and a pharmaceutically acceptable salt of a compound according to Formulae (I)-(V) or a combination thereof.

"Modulating," as used herein, refers to the ability of a compound of the invention to activate and/or inhibit a potassium channel, preferably, a KCNQ potassium channel.

"Opening" and "activating" are used interchangeably herein to refer to the partial or full activation of a KCNQ channel by a compound of the invention, which leads to an increase in ion flux either into or out of a cell in which a KCNQ channel is found.

Where substituent groups are specified by their conventional chemical formulae, written from left to right, they equally encompass the chemically identical substituents which would result from writing the structure from right to left, e.g., —$CH_2O$— is intended to also recite —$OCH_2$—; —$NHS(O)_2$— is also intended to represent. —$S(O)_2HN$—, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)-CH_3$, $-CH_2-CH_2-S(O)_2-CH_3$, $-CH=CH-O-CH_3$, $-Si(CH_3)_3$, $-CH_2-CH=N-OCH_3$, and $-CH=CH-N(CH_3)-CH_3$. Up to two heteroatoms may be consecutive, such as, for example, $-CH_2-NH-OCH_3$ and $-CH_2-O-Si(CH_3)_3$. Similarly, the term "heteroalkylene" by itself or as part of another substituent means a divalent radical derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ represents both $-C(O)_2R'-$ and $-R'C(O)_2-$.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: $-OR'$, $=O$, $=NR'$, $=N-OR'$, $-NR'R''$, $-SR'$, -halogen, $-SiR'R''R'''$, $-OC(O)R'$, $-C(O)R'$, $-CO_2R'$, $-CONR'R''$, $-OC(O)NR'R''$, $-NR''C(O)R'$, $-NR'-C(O)NR''R'''$, $-NR''C(O)_2R'$, $-NR-C(NR'R'')=NR'''$, $-S(O)R'$, $-S(O)_2R'$, $-S(O)_2NR'R''$, $-NRSO_2R'$, $-CN$ and $-NO_2$ in a number ranging from zero to $(2m'+1)$, where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, $-NR'R''$ is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., $-CF_3$ and $-CH_2CF_3$) and acyl (e.g., $-C(O)CH_3$, $-C(O)CF_3$, $-C(O)CH_2OCH_3$, and the like).

Similar to the substituents described for the alkyl radical, substituents for the aryl and heteroaryl groups are varied and are selected from, for example: halogen, $-OR'$, $=O$, $=NR'$, $=N-OR'$, $-NR'R''$, $-SR'$, -halogen, $-SiR'R''R'''$, $-OC(O)R'$, $-C(O)R'$, $-CO_2R'$, $-CONR'R''$, $-OC(O)NR'R''$, $-NR''C(O)R'$, $-NR'-C(O)NR''R'''$, $-NR''C(O)_2R'$, $-NR-C(NR'R'')=NR'''$, $-S(O)R'$, $-S(O)_2R'$, $-S(O)_2NR'R''$, $-NRSO_2R'$, $-CN$ and $-NO_2$, $-R'$, $-N_3$, $-CH(Ph)_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, $(C_1-C_8)$alkyl and heteroalkyl, unsubstituted aryl and heteroaryl, (unsubstituted aryl)-$(C_1-C_4)$alkyl, and (unsubstituted aryl)oxy-$(C_1-C_4)$alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted $(C_1-C_6)$alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfinuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The symbol $\xi$ denotes a point of attachment of a moiety to the remainder of a molecule.

Introduction

The present invention provides compounds which, inter alia, are useful in the treatment of diseases through the modulation of potassium ion flux through voltage-dependent potassium channels. More particularly, the invention provides compounds, compositions and methods that are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety and motor neuron diseases), and as neuroprotective agents (e.g., to prevent stroke and the like). Compounds of the invention have use as agents for treating convulsive states, for example that following grand mal, petit mal, psychomotor epilepsy or focal seizure. The compounds of the invention are also useful in treating disease states such as gastroesophogeal reflux disorder and gastrointestinal hypomotility disorders.

The compounds of the invention are also useful in the treatment, prevention, inhibition and amelioration of urge urinary incontinence also known as bladder instability, neurogenic bladder, voiding dysfunction, hyperactive bladder or detrusor overactivity. The methods of this invention also include the prevention and treatment of mixed stress and urge urinary incontinence, including that associated with secondary conditions such as prostate hypertrophy. The methods of this invention are useful for inducing, assisting or maintaining desirable bladder control in a mammal experiencing or susceptible to bladder instability or urinary incontinence. These methods include prevention, treatment or inhibition of bladder-related urinary conditions and bladder instability, including idiopathic bladder instability, nocturnal enuresis, nocturia, voiding dysfunction and urinary incontinence. Also treatable or preventable with the methods of this invention is bladder instability secondary to prostate hypertrophy. The compounds described herein are also useful in promoting the temporary delay of urination whenever desirable. The compounds of this invention may also be utilized to stabilize the bladder and treat or prevent incontinence which urge urinary incontinence, stress urinary incontinence or a combination of urge and stress incontinence in a mammal, which may also be referred to as mixed urge and stress incontinence. These methods include assistance in preventing or treating urinary incontinence associated with secondary conditions such as prostate hypertrophy. These methods may be utilized to allow a recipient to control the urgency and frequency of urination. The methods of this invention include the treatment, prevention, inhibition and amelioration of urge urinary incontinence also known as bladder instability, neurogenic-bladder, voiding dysfunction, hyperactive bladder, detrusor overactivity, detrusor hyper-reflexia or uninhibited bladder.

As described above, methods of this invention include treatments, prevention, inhibition or amelioration of hyperactive or unstable bladder, neurogenic bladder, sensory bladder urgency, or hyperreflexic bladder. These uses include, but are not limited to, those for bladder activities and instabilities in which the urinary urgency is associated with prostatitis, prostatic hypertrophy, interstitial cystitis, urinary tract infections or vaginitis. The methods of this invention may also be used to assist in inhibition or correction of the conditions of Frequency-Urgency Syndrome, and lazy bladder, also known as infrequent voiding syndrome. The methods of this invention may also be used to treat, prevent, inhibit, or limit the urinary incontinence, urinary instability or urinary urgency associated with or resulting from administrations of other medications, including diuretics, vasopressin antagonists, anticholinergic agents, sedatives or hypnotic agents, narcotics, alpha-adrenergic agonists, alpha-adrenergic antagonists, or calcium channel blockers.

Moreover, compounds of the invention are useful in the treatment of pain, for example, neuropathic pain, inflammatory pain, cancer pain, migraine pain, and musculoskeletal pain. The compounds are also useful to treat conditions, which may themselves be the origin of pain, for example, inflammatory conditions, including arthritic conditions (e.g., rheumatoid arthritis, rheumatoid spondylitis, osteoarthritis and gouty arthritis) and non-articular inflammatory conditions (e.g., herniated, ruptured and prolapsed disc syndrome, bursitis, tendonitis, tenosynovitis, fibromyalgia syndrome, and other conditions associated with ligamentous sprain and regional musculoskeletal strain). Particularly preferred compounds of the invention are less ulcerogenic than other anti-inflammatory agents (e.g., ibuprofen, naproxen and aspirin). Furthermore, the compounds of the invention are useful in treating conditions and pain associated with abnormally raised skeletal muscle tone.

The compounds of the invention are also of use in treating anxiety (e.g. anxiety disorders). Anxiety disorders are defined in the Diagnostic and Statistical Manual of Mental Disorders (Third Edition-revised 1987, published by the American Psychiatric Association, Washington, D.C., see, pages 235 to 253), as psychiatric conditions having symptoms of anxiety and avoidance behavior as characteristic features. Included amongst such disorders are generalized anxiety disorder, simple phobia and panic disorder.

Anxiety also occurs as a symptom associated with other psychiatric disorders, for example, obsessive compulsive disorder, post-traumatic stress disorder, schizophrenia, mood disorders and major depressive disorders, and with organic clinical conditions including, but not limited to, Parkinson's disease, multiple sclerosis, and other physically incapacitating disorders.

In view of the above-noted discovery, the present invention provides compounds, compositions, and methods for increasing ion flux in voltage-dependent potassium channels, particularly those channels responsible for the M-current. As used herein, the term "M-current," "channels responsible for the M-current" and the like, refers to a slowly activating, non-inactivating, slowly deactivating voltage-gated $K^+$ channel. M-current is active at voltages close to the threshold for action potential generation in a wide variety of neuronal cells, and thus, is an important regulator of neuronal excitability.

Recently, members of the voltage-dependent potassium channel family were shown to be directly involved in diseases of the central or peripheral nervous system. The fused ring heterocycles provided herein are now shown to act as potassium channel modulators.

DESCRIPTION OF THE EMBODIMENTS

I. Modulators of Voltage-Dependent Potassium Channels

In one aspect, the present invention provides compounds of the formula:

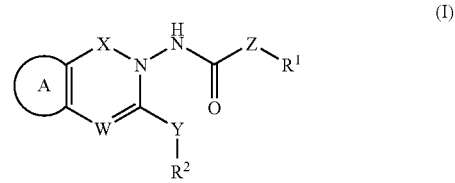

in which the symbol A represents a ring system such as a five- or six-membered substituted or unsubstituted aryl, a five- and six-membered substituted or unsubstituted heteroaryl, a substituted or unsubstituted $C_4$-$C_8$ cycloalkyl, or a substituted or unsubstituted 5-8 membered heterocyclyl.

In an exemplary embodiment, A is substituted or unsubstituted phenyl. Exemplary substituted phenyl moieties include those that are substituted with one or two groups that are independently selected from halogen, nitrile, substituted or unsubstituted $C_1$-$C_4$ alkyl, $SCF_3$, trifluoromethyl and trifluoromethoxy. In another exemplary embodiment, A is substituted or unsubstituted 5- or 6-membered heteroaryl.

X is a moiety such as CO, CS or $SO_2$. The symbol W represents N or $CR^3$, in which $R^3$ is H, F, substituted or unsubstituted aryl, substituted or unsubstituted heteroaryl, substituted or unsubstituted $C_3$-$C_8$ cycloalkyl, substituted or unsubstituted 5-7 membered heterocyclyl, or substituted or unsubstituted $C_1$-$C_8$ alkyl.

The symbol Z indicates a bond, —$CH_2$—, —CHF—, —$CF_2$—, —CH=CH— or —$NR^4(CR^{4a}R^{4b})_s$—, wherein $R^4$ is a member selected from H and a substituted or unsubstituted $C_1$-$C_5$ alkyl group. The symbols $R^{4a}$ and $R^{4b}$ represent groups that are independently selected from H, substituted or unsubstituted aryl, substituted or unsubstituted heteroaryl, substituted or unsubstituted $C_3$-$C_8$ cycloalkyl, substituted or unsubstituted 5-7 membered heterocyclyl, or substituted or unsubstituted $C_1$-$C_8$ alkyl. The symbol s represents an integer from 1 to 3; Y represents $(CR^5R^6)_n$, in which n is an integer from 0-4. In a preferred embodiment, when n is 0 and $R^2$ is methyl, A is not an unsubstituted phenyl moiety.

$R^5$ and $R^6$ independently represent H, F, substituted or unsubstituted aryl, substituted or unsubstituted heteroaryl, substituted or unsubstituted $C_3$-$C_8$ cycloalkyl, substituted or unsubstituted 5-7 membered heterocyclyl, or substituted or unsubstituted $C_1$-$C_8$ alkyl.

The symbol $R^1$ represents a moiety that is selected from substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl.

In an exemplary embodiment, $R^1$ is substituted or unsubstituted phenyl. When $R^1$ is substituted phenyl, it is preferably substituted by one or more independently selected moiety, such as substituted or unsubstituted $C_1$-$C_8$ alkyl, substituted or unsubstituted 2 to 8 membered heteroalkyl, halogen, CN, $CF_3$ or $OCF_3$.

$R^2$ is $CF_3$, substituted or unsubstituted $C_1$-$C_8$ alkyl, substituted or unsubstituted aryl, substituted or unsubstituted heteroaryl, substituted or unsubstituted $C_3$-$C_8$ cycloalkyl, substituted or unsubstituted 3-7-membered heterocyclyl. $R^2$ is preferably a substituted or unsubstituted $C_1$-$C_6$ acyclic alkyl group, more preferably a $C_1$-$C_4$ saturated acyclic alkyl group or $CF_3$. In some related embodiments, Y is —$CF_2$— or n is 0.

In an exemplary embodiment, when X is C(O); and A is unsubstituted phenyl or 1,3-benzodioxolyl or 6-halophenyl; and W is N; and Y—$R^2$ is unsubstituted acyclic alky, acyclic alkyl substituted with an amide or unsubstituted phenyl, then Z-$R^1$ is other than acyclic alkyl substituted with unsubstituted phenyl, acyclic alkylene substituted with unsubstituted phenyl and acyclic alkyl substituted with 4-phenyl-1-halo. In preferred embodiments of compounds according to the above proviso, Y—$R^2$ is acyclic $C_1$-$C_4$ linear alkyl or $C_1$-$C_4$ branched alkyl, e.g., methyl, ethyl, and isopropyl. In still further preferred embodiments according to the above proviso, Z-$R^1$ is other than unsubstituted benzyl, unsubstituted phenethyl. In another preferred embodiment, Z-$R^1$ is other than —CH=CH-phenyl.

In another exemplary embodiment, A is selected from substituted or unsubstituted pyrazolyl, substituted or unsubstituted imidazolyl, substituted or unsubstituted thiazolyl, substituted or unsubstituted oxazolyl, substituted or unsubstituted triazolyl, substituted or unsubstituted isothiazolyl, substituted or unsubstituted isoxazolyl, and substituted or unsubstituted 1,2,3,-oxadiazolyl. A may also be selected from substituted or unsubstituted pyrazolyl or substituted or unsubstituted imidazolyl.

In a related embodiment, A is substituted with $R^8$ and $R^9$, wherein $R^8$ and $R^9$ are independently selected from: H, halo, $CF_3$, $CF_3O$, $NO_2$, CN, $S(O)_mR^{10}$, $COOR^{11}$, $CONR^{12}R^{13}$, $SO_2NR^{12}R^{13}$, $S(O)_nCF_3$, $CH_2CF_3$, substituted or unsubstituted $C_1$-$C_6$ alkyl, and substituted or unsubstituted $C_3$-$C_7$ cycloalkyl. $R^{10}$ and $R^{11}$ are independently selected from substituted or unsubstituted $C_1$-$C_5$ alkyl, and substituted or unsubstituted $C_3$-$C_7$ cycloalkyl. The symbol m represents an integer from 0 to 2. $R^{12}$ and $R^{13}$ are independently selected from H, substituted or unsubstituted $C_1$-$C_5$ alkyl, and substituted or unsubstituted $C_3$-$C_7$ cycloalkyl. $R^{12}$ and $R^{13}$ are optionally joined together with the nitrogen atom to which they are attached to form a 5- to 7-membered ring.

In some embodiments, A has the formula:

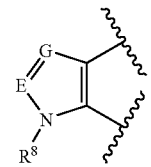

(II)

In Formula (II), E is $CR^9$ and G is N, or E is N and G is $CR^9$. $R^8$ and $R^9$ may be independently selected from $CF_3$, substituted or unsubstituted $C_1$-$C_6$ alkyl, substituted or unsubstituted $C_3$-$C_7$ cycloalkyl, $OCF_3$ and $CH_2CF_3$.

In other embodiments, A has the formula:

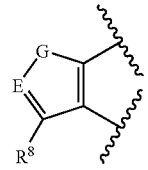

(III)

In Formula (III), E is selected from $CR^9$ and N, and G is selected from O and S. $R^8$ and $R^9$ are independently selected from $CF_3$, substituted or unsubstituted $C_1$-$C_6$ alkyl, substituted or unsubstituted $C_3$-$C_7$ cycloalkyl, $OCF_3$, and $CH_2CF_3$.

In exemplary embodiments related to compounds with A having Formula (II) or (III), X is a member selected from CO and $SO_2$; Z is $CH_2$; W is N; and $R^1$ is substituted or unsubstituted phenyl. In other related embodiments, $R^2$ is a member selected from substituted or unsubstituted $C_1$-$C_4$ alkyl, substituted or unsubstituted $C_3$-$C_6$ cycloalkyl and substituted or unsubstituted $C_3$-$C_6$ heterocyclyl. $R^8$ and $R^9$ may be independently selected from H, halo, $CF_3$, $OCF_3$, substituted or unsubstituted $C_1$-$C_5$ alkyl, $SCF_3$, $CH_2CF_3$ and CN. Y may be —$CF_2$— or n is 0.

In another exemplary embodiment, the invention provides a compound having the formula:

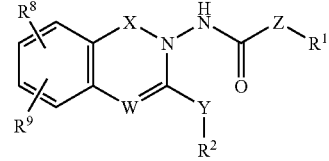

(IV)

in which the symbols $R^8$ and $R^9$ independently represent H, halo, $CF_3$, $CF_3O$, $NO_2$, CN, $S(O)_mR^{10}$, $COOR^{11}$, $CONR^{12}R^{13}$, $SO_2NR^{12}R^{13}$, $S(O)_mCF_3$, substituted or unsubstituted $C_1$-$C_6$ alkyl, or substituted or unsubstituted $C_3$-$C_7$ cycloalkyl. $R^{10}$ and $R^{11}$ independently represent substituted or unsubstituted $C_1$-$C_5$ alkyl, or substituted or unsubstituted $C_3$-$C_7$ cycloalkyl. The symbol m represents an integer from 0 to 2. $R^{12}$ and $R^{13}$ are independently H, substituted or unsubstituted $C_1$-$C_5$ alkyl, or substituted or unsubstituted $C_3$-$C_7$ cycloalkyl. $R^{12}$ and $R^{13}$, together with the nitrogen atom to which they are attached, optionally form a 5- to 7-membered ring. The identities of the remaining variable groups are substantially identical to their counterparts discussed hereinabove.

In an exemplary embodiment, $R^8$ and $R^9$ are independently selected from H, halo, $CF_3$, $OCF_3$, substituted or unsubstituted $C_1$-$C_8$ alkyl, $SCF_3$, $CH_2CF_3$ and CN. In another exemplary embodiment, Y is —$CF_2$— or n is 0. $R^2$ may be a member selected from substituted or unsubstituted $C_1$-$C_4$ alkyl, substituted or unsubstituted $C_1$-$C_6$ cycloalkyl and substituted or unsubstituted $C_1$-$C_6$ heterocyclyl.

Exemplary compounds of the invention in which X is C(O); $R^8$ and $R^9$ are both H or $R^8$ is 6-halophenyl and $R^9$ is H or $R^8$ and $R^9$ taken together with the carbon atoms to which they are joined form a dioxolyl ring; W is N; and Y—$R^2$ is unsubstituted acyclic alkyl, acyclic alkyl substituted with an amide or unsubstituted phenyl, have a Z-$R^1$ group that is other than acyclic alkyl substituted with unsubstituted phenyl, acyclic alkylene substituted with unsubstituted phenyl and acyclic alkyl substituted with 4-phenyl-1-halo.

Another exemplary embodiment of the invention provides compounds having the formula:

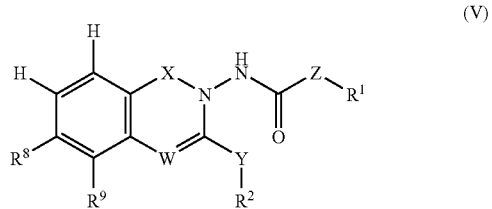

(V)

in which the identity of each variable moiety is substantially identical to its counterpart discussed above in reference to Formula (IV).

In certain preferred compounds according to Formulae (IV) and (V), $R^2$ is a member selected from substituted or unsubstituted $C_1$-$C_4$ alkyl, substituted or unsubstituted $C_1$-$C_6$ cycloalkyl and substituted or unsubstituted $C_1$-$C_6$ heterocyclyl; and $R^8$ and $R^9$ are optionally members independently selected from H, halo, $CF_3$, $OCF_3$, substituted or unsubstituted $C_1$-$C_5$ alkyl, $SCF_3$, $CH_2CF_3$ and CN. In another exemplary embodiment, Y is —$CF_2$— or n is 0. In related embodiments, X is CO; $R^8$ is H; $R^9$ is $CF_3$; n is 0; $R^2$ is $C_1$-$C_4$ alkyl; and $R^1$ is phenyl substituted with a halo.

Exemplary compounds of the invention have Z-$R^1$ groups that are other than acyclic alkyl substituted with unsubstituted phenyl, acyclic alkylene substituted with unsubstituted phenyl and acyclic alkyl substituted with 4-phenyl-1-halo when X is C(O); $R^8$ and $R^9$ are both H; W is N; and Y—$R^2$ is unsubstituted acyclic alkyl, acyclic alkyl substituted with an amide or unsubstituted phenyl.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention, or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds within the motif set forth in Formula I, which are functionalized to afford compounds having a water-solubility that is enhanced relative to analogous compounds that are not similarly functionalized. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

Preparation of Potassium Channel Modulators

The method by which the compounds of the invention are prepared is not critical; any synthetic pathway that leads to the desired compounds is of use to prepare fused ring heterocycles that are within the scope of the invention set forth herein.

In an exemplary reaction pathway, fused ring heterocycles of the invention are prepared by cyclizing an anthranilic acid. Substituted anthranilic acid precursors were prepared and cyclized and the cyclized products optionally elaborated following the method outlined in Scheme 1.

Scheme 1

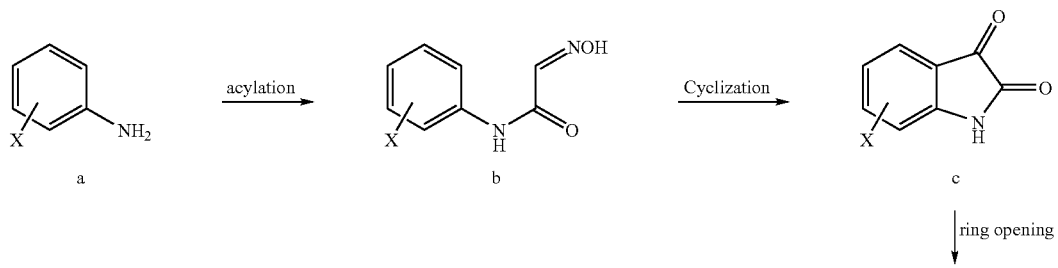

ring opening

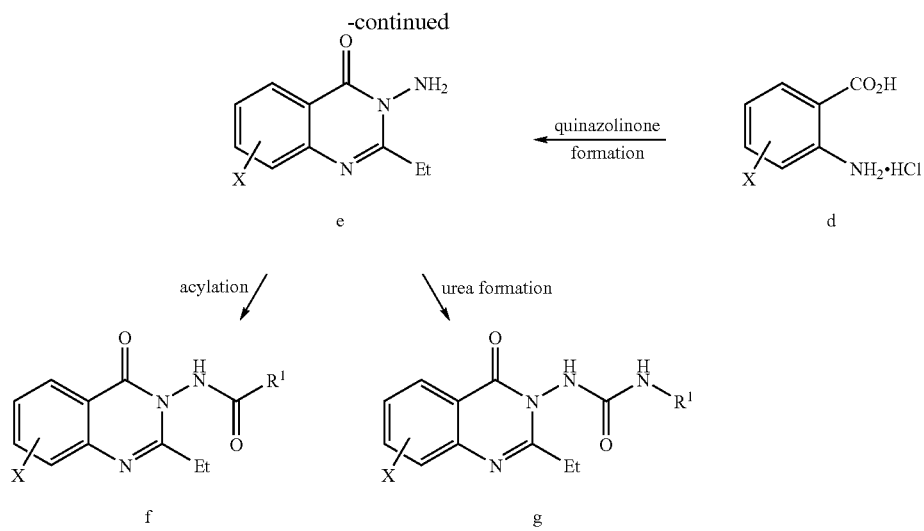

Substituted aniline a is chain-extended to form the intermediate α-oximinoanilides b using chloral hydrate and hydroxylamine. Treatment of these intermediates with strong acid at elevated temperatures facilitates the desired ring closure to generate the substituted isatins c. Selective ring opening of the isatins using sodium hydroxide and hydrogen peroxide provides the desired anthranilic acids d. According to the present scheme, a two-step one-pot procedure is used to convert the substituted anthranilic acids into the versatile substituted 3-amino-3H-quinazolin-4-ones e. The final products f and g were obtained by either acylating the free amino group to generate the appropriate amides or by reacting the free amine with an isocyanate to yield the corresponding urea.

The 3-amino-substituted fused ring heterocycles of the invention are readily formed by methods such as that set forth in Scheme 2 in which d is cyclized to the corresponding quinazolinone e.

Scheme 2

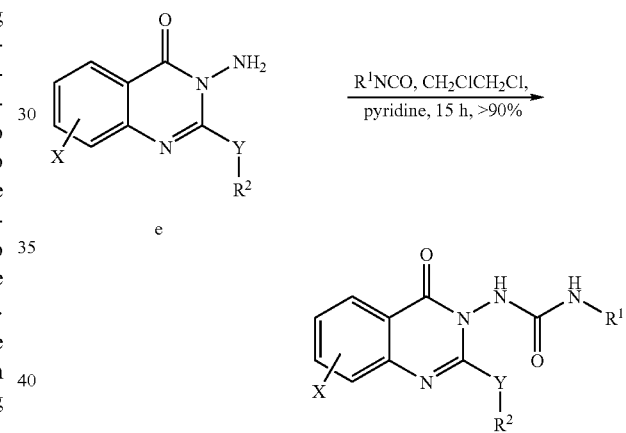

The amine moiety can be elaborated by methods such as that set forth in Scheme 3, showing a general preparative route for converting a 3-aminoquinazolinone into the corresponding urea quinazolinone g.

Scheme 3

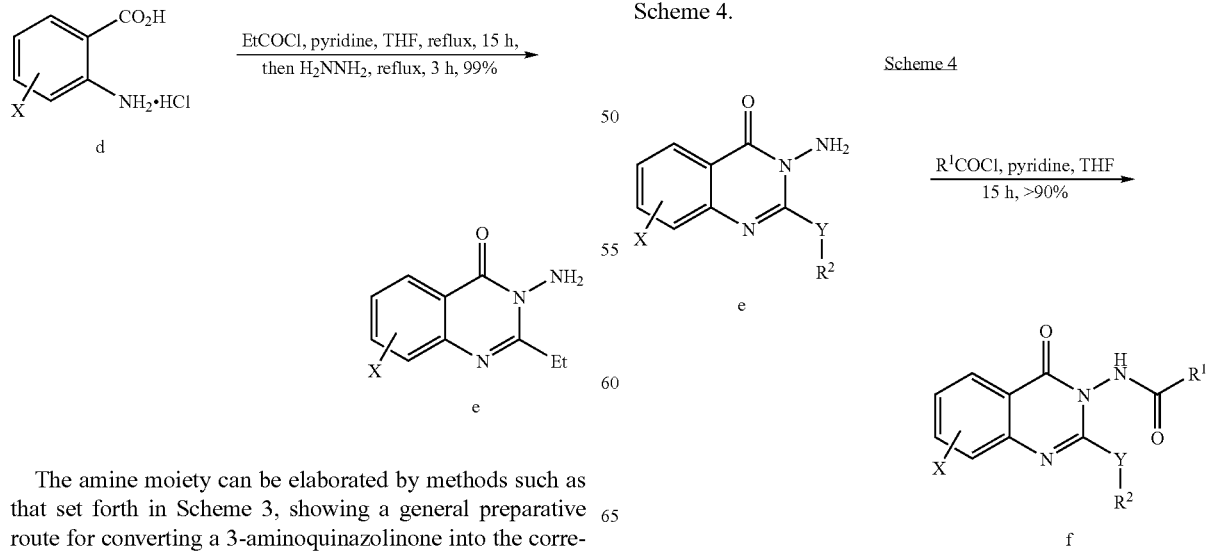

The amine moiety of the 3-aminoquinazolinone e is also readily converted to the corresponding amide f according to Scheme 4.

Scheme 4

Alternatively, the amides of the invention are prepared according to the route set forth in Scheme 5.

Scheme 5

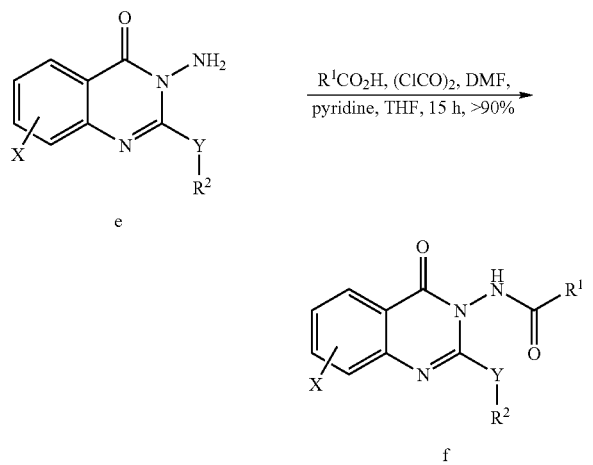

As shown in Scheme 6, another useful synthetic route to quinazolinone amides begins with an anthranilic acid d, which is converted to isatoic anhydride. The corresponding acylhydrazide k is produced by opening the cyclic anhydride with the desired hydrazide. Quinazolinone amide f is formed by forming a ring between an amine of the hydrazide moiety and the aniline nitrogen.

In an alternate route, also according to Scheme 6, the carboxylic acid of nitrobenzoic acid i is activated and the activated agent used to acylate a hydrazide, forming nitrobenzyl hydrazide j, the nitro group of which is reduced, forming the corresponding acylhydrazide k.

Scheme 6

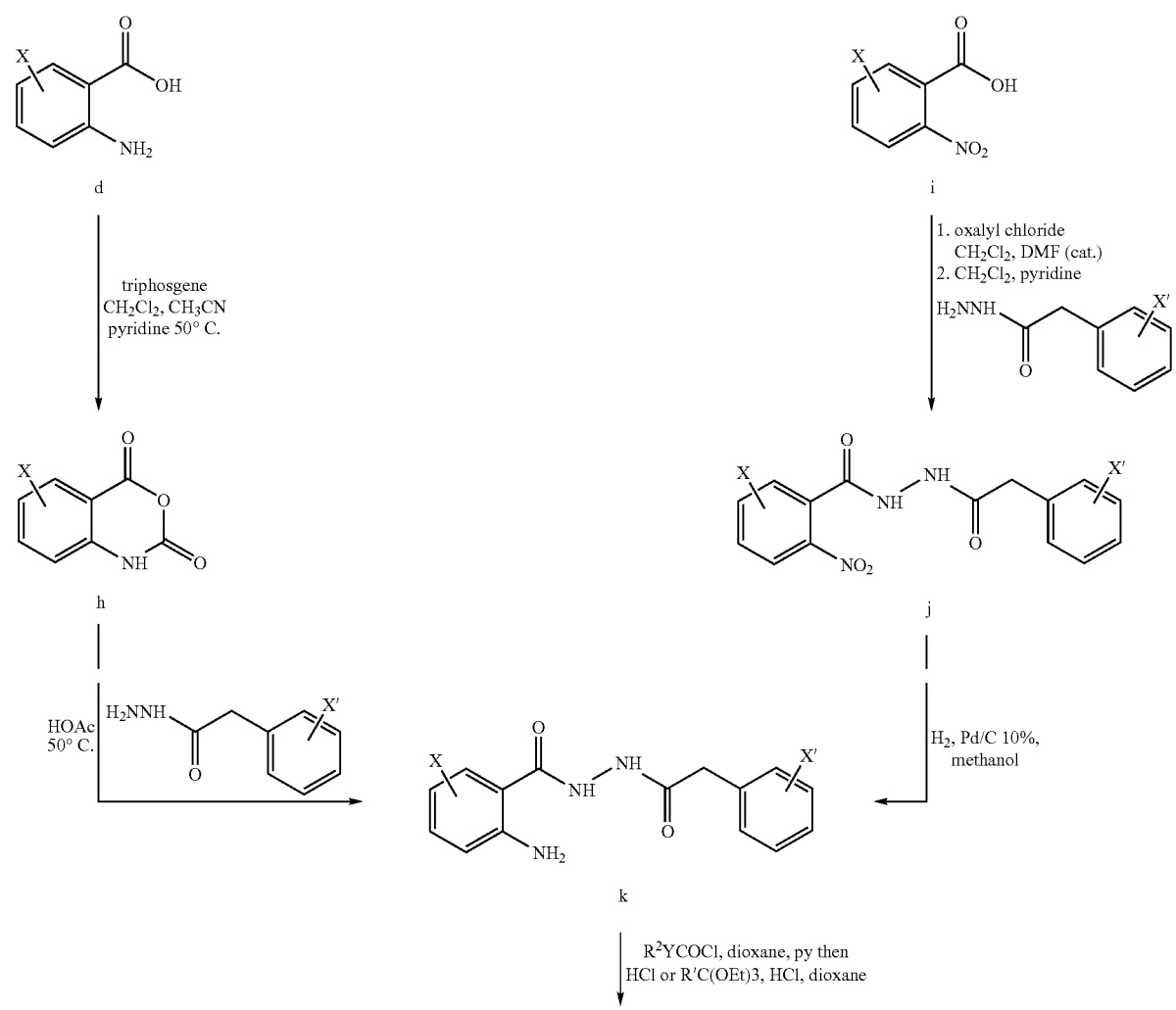

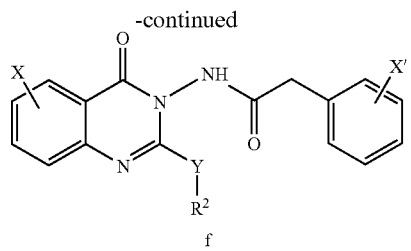

f

The 1,1-dioxo-1H-1λ⁶-benzo[1,2,4]thiadiazin-2-yl compounds of the invention can be prepared by the method of Scheme 7, beginning with a nitrosulfonyl chloride 1. The chloride is displaced by a hydrazide, forming m. The nitro group is reduced, providing aniline n, the amine of which is subsequently displaced, forming o.

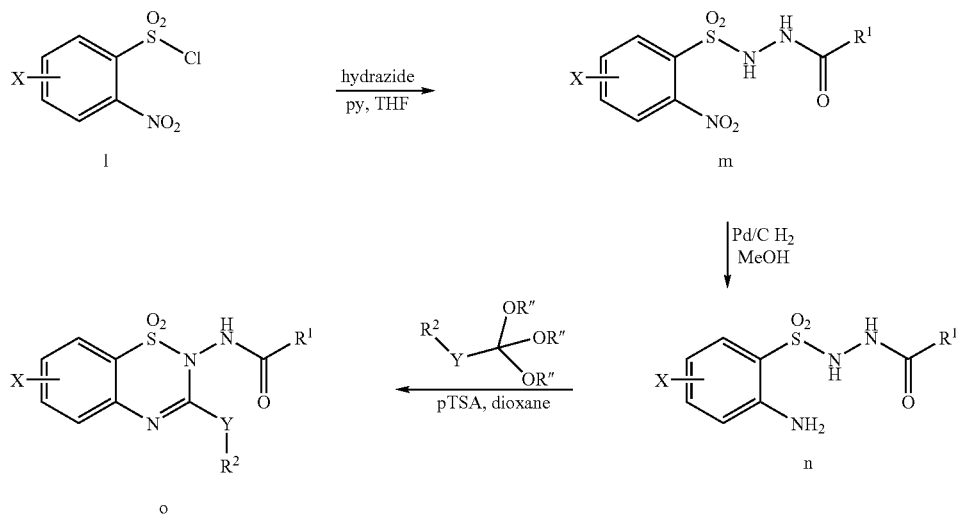

Methods for preparing dimers, trimers and higher homologs of small organic molecules, such as those of the present invention, as well as methods of functionalizing a polyfunctional framework molecule are well known to those of skill in the art. For example, an aromatic amine of the invention is converted to the corresponding isothiocyanate by the action of thiophosgene. The resulting isothiocyanate is coupled to an amine of the invention, thereby forming either a homo- or heterodimeric species. Alternatively, the isothiocyanate is coupled with an amine-containing backbone, such as polylysine, thereby forming a conjugate between a polyvalent framework and a compound of the invention. If it is desired to prepare a hetereofuntionalized polyvalent species, the polylysine is underlabeled with the first isothiocyanate and subsequently labeled with one or more different isothiocyanates. Alternatively, a mixture of isothiocyanates is added to the backbone. Purification proceeds by, for example, size exclusion chromatography, dialysis, nanofiltration and the like.

Exemplary methods for producing 5-membered fused ring heterocycles are presented in Example 6 below. One of skill in the art will immediately recognize that compounds having a wide variety of 5-membered heterocycles may be synthesized by elaboration of the disclosed synthesis methods.

In Schemes 1-7 above and 8-15 below, the symbol X represents at least on moiety equivalent to $R^8$ and/or $R^9$ as discussed above; the symbol X" represents at least one moiety independently selected from substituted or unsubstituted $C_1$-$C_8$ alkyl, substituted or unsubstituted 2 to 8 membered heteroalkyl, halogen, CN, $CF_3$ or $OCF_3$; $R^1$, $R^2$, and Y are as described above in the discussion of the modulator compositions.

II. Assays for Modulators of KCNQ Channels

Assays for determining the ability of a compound of the invention to open a potassium ion channel are generally known in the art. One of skill in the art is able to determine an appropriate assay for investigating the activity of a selected compound of the invention towards a particular ion channel. For simplicity, portions of the following discussion focuses on KCNQ2 as a representative example, however, the discussion is equally applicable to other potassium ion channels.

KCNQ monomers as well as KCNQ alleles and polymorphic variants are subunits of potassium channels. The activity of a potassium channel comprising KCNQ subunits can be assessed using a variety of in vitro and in vivo assays, e.g., measuring current, measuring membrane potential, measuring ion flux, e.g., potassium or rubidium, measuring potassium concentration, measuring second messengers and transcription levels, using potassium-dependent yeast growth assays, and using e.g., voltage-sensitive dyes, radioactive tracers, and patch-clamp electrophysiology.

Furthermore, such assays can be used to test for activators of channels comprising KCNQ. As discussed elsewhere herein, activators (openers) of a potassium channel are useful for treating various disorders attributable to potassium channels. Such modulators are also useful for investigation of the channel diversity provided by KCNQ and the regulation/modulation of potassium channel activity provided by KCNQ.

Putative modulators of the potassium channels are tested using biologically active KCNQ, either recombinant or naturally occurring, or by using native cells, like cells from the nervous system expressing the M-current. KCNQ can be isolated, co-expressed or expressed in a cell, or expressed in a membrane derived from a cell. In such assays, KCNQ2 is expressed alone to form a homomeric potassium channel or is co-expressed with a second subunit (e.g., another KCNQ family member, preferably KCNQ3) so as to form a heteromeric potassium channel. Modulation is tested using one of the in vitro or in vivo assays described above. Samples or assays that are treated with a potential potassium channel activator are compared to control samples without the test compound, to examine the extent of modulation. Control samples (untreated with activators) are assigned a relative potassium channel activity value of 100. Activation of channels comprising KCNQ2 is achieved when the potassium channel activity value relative to the control is 110%, more preferably 130%, more preferably 170% higher. Compounds that increase the flux of ions will cause a detectable increase in the ion current density by increasing the probability of a channel comprising KCNQ2 being open, by decreasing the probability of it being closed, by increasing conductance through the channel, and/or increasing the number or expression of channels.

Changes in ion flux may be assessed by determining changes in polarization (i.e., electrical potential) of the cell or membrane expressing the potassium channel comprising, for example, KCNQ2, KCNQ2/3 or the M-current. A preferred means to determine changes in cellular polarization is by measuring changes in current or voltage with the voltage-clamp and patch-clamp techniques, using the "cell-attached" mode, the "inside-out" mode, the "outside-out" mode, the "perforated cell" mode, the "one or two electrode" mode, or the "whole cell" mode (see, e.g., Ackerman et al., *New Engl. J. Med.* 336:1575-1595 (1997)). Whole cell currents are conveniently determined using the standard methodology (see, e.g., Hamil et al., *Pflugers. Archiv.* 391:85 (1981). Other known assays include: radiolabeled rubidium flux assays and fluorescence assays using voltage-sensitive dyes (see, e.g., Vestergarrd-Bogind et al., *J. Membrane Biol.* 88:67-75 (1988); Daniel et al., *J. Pharmacol. Meth.* 25:185-193 (1991); Holevinsky et al., *J. Membrane Biology* 137:59-70 (1994)). Assays for compounds capable of increasing potassium flux through M-current channels found in native cells or through the channel proteins comprising KCNQ2 or heteromultimers of KCNQ subunits can be performed by application of the compounds to a bath solution in contact with and comprising cells having a channel of interest (see, e.g., Blatz et al., *Nature* 323:718-720 (1986); Park, *J. Physiol.* 481:555-570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The cations can be measured in a variety of standard ways. They can be measured directly by concentration changes of the ions or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $Ca^{2+}$, or cyclic nucleotides.

KCNQ2 orthologs will generally confer substantially similar properties on a channel comprising such KCNQ2, as described above. In a preferred embodiment, the cell placed in contact with a compound that is suspected to be a KCNQ2 homolog is assayed for increasing or decreasing ion flux in a eukaryotic cell, e.g., an oocyte of *Xenopus* (e.g., *Xenopus laevis*) or a mammalian cell such as a CHO or HeLa cell. Channels that are affected by compounds in ways similar to KCNQ2 are considered homologs or orthologs of KCNQ2.

Utilizing screening assays such as described above, compounds of the invention were tested for their ability to open voltage-gated potassium channels. The results of these assays are set forth in Table 1 in which the data are presented in terms of relative potency of the compounds tested to one another. The compound numbers in Table 1 are cross-referenced to the compounds displayed in FIG. 1

III. Pharmaceutical Compositions of Potassium Channel Modulators

In another aspect, the present invention provides pharmaceutical compositions comprising a pharmaceutically acceptable excipient and a compound of Formulae (I)-(V) provided above.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of Formula I, or a pharmaceutically acceptable salt thereof.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat pain or anxiety, such compositions will contain an amount of active ingredient effective to achieve a clinically relevant degree of reduction in the condition being treated. Similarly, when the pharmaceutical composition is used to treat or prevent a central or peripheral nervous system disorder, e.g., Parkinson's disease a therapeutically effective amount will reduce one or more symptoms characteristic of the diseases (e.g., tremors) to below a predetermined pressure threshold. Determination of a therapeutically effective amount of a compound of the invention is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of modulating, e.g., activating or opening the KCNQ channel. In preferred embodiments, the KCNQ channel activity is altered by at least 30%. Target plasma concentrations of active compound(s) that are capable of inducing at least about 50%, 70%, or even 90% or higher alteration of the KCNQ channel potassium flux are presently preferred. The percentage of alteration of the KCNQ channel in the patient can be monitored to assess the appropriateness of the plasma drug concentration achieved, and the dosage can be adjusted upwards or downwards to achieve the desired percentage of alteration.

As is well known in the art, therapeutically effective amounts for use in humans can also be determined from animal models. For example, a dose for humans can be formulated to achieve a circulating concentration that has been found to be effective in animals. A particularly useful animal model for predicting anticonvulsant dosages is the maximal electroshock assay (Fischer R S, *Brain Res. Rev.* 14: 245-278 (1989)). The dosage in humans can be adjusted by monitoring KCNQ channel activation and adjusting the dosage upwards or downwards, as described above.

A therapeutically effective dose can also be determined from human data for compounds which are known to exhibit similar pharmacological activities, such as retigabine (Rudnfeldt et al., *Neuroscience Lett.* 282: 73-76 (2000)).

Adjusting the dose to achieve maximal efficacy in humans based on the methods described above and other methods as are well-known in the art is well within the capabilities of the ordinarily skilled artisan.

By way of example, when a compound of the invention is used in the prophylaxis and/or treatment of an exemplary disease such as epilepsy, a circulating concentration of administered compound of about 0.001 µM to 20 µM is considered to be effective, with about 0.01 µM to 5 µM being preferred.

Patient doses for oral administration of the compounds described herein, which is the preferred mode of administration for prophylaxis and for treatment of an exemplary disease such as epilepsy, typically range from about 1 mg/day to about 10,000 mg/day, more typically from about 10 mg/day to about 1,000 mg/day, and most typically from about 1 mg/day to about 500 mg/day. Stated in terms of patient body weight, typical dosages range from about 0.01 to about 150 mg/kg/day, more typically from about 0.1 to about 15 mg/kg/day, and most typically from about 0.5 to about 10 mg/kg/day.

For other modes of administration, dosage amount and interval can be adjusted individually to provide plasma levels of the administered compound effective for the particular clinical indication being treated. For example, if acute epileptic seizures are the most dominant clinical manifestation, in one embodiment, a compound according to the invention can be administered in relatively high concentrations multiple times per day. Alternatively, if the patient exhibits only periodic epileptic seizures on an infrequent, periodic or irregular basis, in one embodiment, it may be more desirable to administer a compound of the invention at minimal effective concentrations and to use a less frequent administration regimen. This will provide a therapeutic regimen that is commensurate with the severity of the individual's disease.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Therapeutic Index

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the EDso with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

IV. Methods for Increasing Ion Flow in Voltage-Dependent Potassium Channels

In yet another aspect, the present invention provides methods for increasing ion flow through voltage dependent potassium channels in a cell. The method includes contacting a cell containing the target ion channels with an amount of a compound of the invention sufficient to enhancer the activity of a potassium channel.

The methods provided in this aspect of the invention are useful for the diagnosis of conditions that can be treated by modulating ion flux through voltage-dependent potassium channels, or for determining if a patient will be responsive to therapeutic agents, which act by opening potassium channels. In particular, a patient's cell sample can be obtained and contacted with a compound of the invention and the ion flux can be measured relative to a cell's ion flux in the absence of a compound of the invention. An increase in ion flux will typically indicate that the patient will be responsive to a therapeutic regimen of ion channel openers.

V. Methods for Treating Conditions Mediated by Voltage-Dependent Potassium Channels In still another aspect, the present invention provides a method for the treatment of a central or peripheral nervous system disorder or condition through modulation of a voltage-dependent potassium channel. In this method, a subject in need of such treatment is administered an effective amount of a compound having the formula provided above.

The compounds provided herein are useful as potassium channel modulators and find therapeutic utility via modulation of voltage-dependent potassium channels in the treatment of diseases or conditions. The potassium channels targets for the compounds of the invention are described herein as voltage-dependent potassium channels such as the KCNQ potassium channels. As noted above, these channels may include homomultimers and heteromultimers of KCNQ2, KCNQ3, KCNQ4, KCNQ5 and KCNQ6. A heteromultimer of two proteins, e.g., KCNQ2 and KCNQ3 is referred to as, for example, KCNQ2/3, KCNQ3/5, etc. The conditions that can be treated with the compounds and compositions of the present invention may include, but are not limited to, central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety, and motor neuron diseases). The compounds and compositions of the present invention may also serve as neuroprotective agents (e.g., to prevent stroke and the like). In a preferred embodiment, the condition or disorder to be treated is epilepsy or seizures. In another preferred embodiment, the condition or disorder is hearing loss.

In therapeutic use for the treatment of epilepsy or other neurological conditions, the compounds utilized in the pharmaceutical method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

EXAMPLES

The following examples are offered to illustrate, but not to limit the claimed invention.

In the examples below, unless otherwise stated, temperatures are given in degrees Celsius (° C.); operations were carried out at room or ambient temperature (typically a range of from about 18-25° C.; evaporation of solvent was carried out using a rotary evaporator under reduced pressure (typically, 4.5-30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours).

Example 1

Example 1 sets forth a general method for preparing 3-amino-substituted fused ring heterocycles from anilines according to Scheme 1.

1.1 Preparation of 2-(Trifluoromethoxy)-α-oximinoanilide

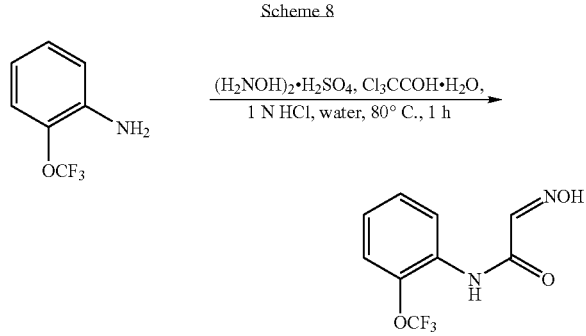

Scheme 8

According to Scheme 8, hydroxylamine sulfate (18 g, 3 equivalents) was dissolved in water (80 mL) and then chloral hydrate (7.3 g, 1.2 equivalents) was added. After 15 min, a solution of the starting aniline (5.0 mL, 37 mmol), dissolved in 1 N HCl (44 mL, 1.2 equivalents), was added dropwise (20 min) to the reaction mixture. The resulting cloudy mixture was heated at 80° C. for 1 h, cooled to rt, and diluted with CHCl$_3$ (160 mL). The aqueous layer was extracted with CHCl$_3$ (2×80 mL). The combined organic layers were dried (Na$_2$SO$_4$), filtered and evaporated. Hexanes (40 mL) were added. Evaporation of the solvent provided crude product which was used in the next step without further purification: MS(ESI): 247 (M–H)$^-$.

1.2 Preparation of 7-(Trifluoromethoxy)isatin

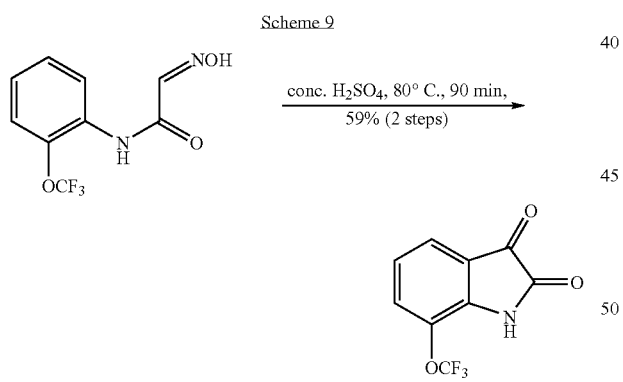

Scheme 9

According to Scheme 9, concentrated sulfuric acid (40 mL) was heated to 65° C. and poured into a flask containing the crude 2-(trifluoromethoxy)-α-oximinoanilide from Example 1.1. The mixture was stirred at 65° C. until homogeneous and then the temperature was increased to 80° C. After 90 min, the resulting black mixture was poured into ice/water (300 mL) and diluted with 15% i-PrOH/CHCl$_3$ (200 mL). After slow addition of 6 N NaOH (80 mL, 15 mins), the aqueous layer was extracted with CHCl$_3$ (2×80 mL). To the combined organic layers was added silica gel (30 g) and the solvent was then evaporated. The resulting solid was applied to a column of silica gel and eluted with 15-25% EtOAc/hexanes to provide the product (5.0 g, 59%, 2 steps): MS(ESI): 230 (M–H)$^-$.

1.3 Preparation of 2-Amino-3-trifluoromethoxybenzoic Acid Hydrogen Chloride

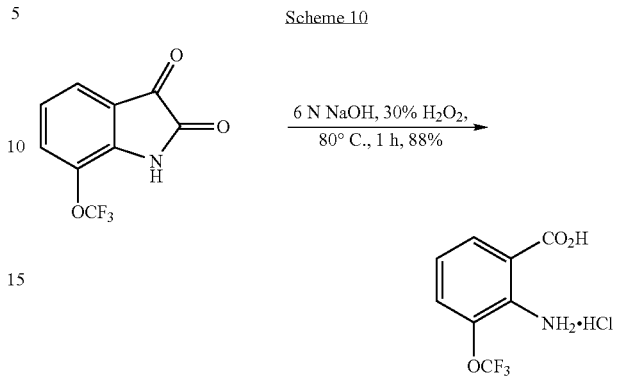

Scheme 10

According to Scheme 10, the starting isatin (3.5 g, 15 mmol) and 6 N NaOH (25 mL, 10 equivalents) were heated at 80° C. and treated slowly with 30% H$_2$O$_2$ (4.5 mL, 0.3 mL/mmol, gas evolution). After 1 h, the mixture was cooled to room temperature and 6 N HCl was added dropwise (27 mL), whereupon a precipitate formed. After 30 mins, the mixture was cooled to 0° C. and the solid was filtered, washed with ice cold water (15 mL) and dissolved in CH$_2$Cl$_2$ (45 mL). The organic solution was dried (Na$_2$SO$_4$), filtered and evaporated to provide the product as an off-white solid (3.4 g, 88%): MS(ESI): 220 (M–H)$^-$.

Preparation of 3-Amino-2-ethyl-8-trifluoromethoxy-3H-quinazolin-4-one

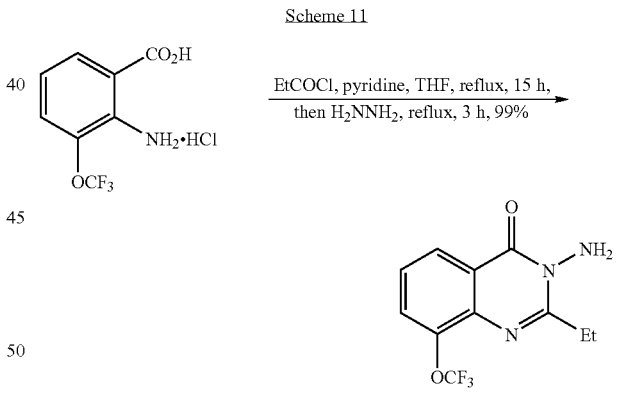

Scheme 11

According to Scheme 11, the starting anthranilic acid (2.1 g, 8.1 mmol) was dissolved in dry THF (40 mL) and treated with pyridine (3.9 mL, 6 equivalents), followed by propionyl chloride (2.9 mL, 4 equivalents, immediate precipitate). The mixture was heated at reflux for 15 h and then cooled to 0° C. before adding hydrazine (3.1 mL, 12 equivalents). This mixture was then heated at reflux for 3 h. Most of the THF was evaporated and the resulting mixture diluted with CHCl$_3$ (40 mL), saturated aqueous NaHCO$_3$ solution (60 mL) and water (20 mL). The aqueous layer was extracted with CHCl$_3$ (2×20 mL). Silica gel (15 g) was added to the combined organic layers and the solvent was then evaporated. The resulting solid was applied to a column of silica gel and eluted with 5-8% MeCN/45-42% hexanes/50% CH$_2$Cl$_2$ to provide the product as an off-white solid (2.2 g, 99%): MS(ESI): 274 (MH$^+$).

Example 2

2.1 General Preparative Method for Urea Fused Ring Heterocycles

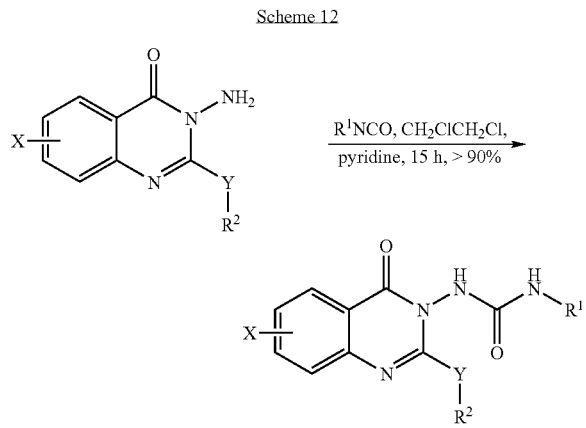

Scheme 12

As shown in Scheme 12, the starting 3-aminoquinazolinone (0.1 mmol) was dissolved in dry CH$_2$ClCH$_2$Cl (1 mL) and treated with pyridine (1.5 equivalents) followed by an isocyanate (1.2 equivalents). After 15 h, saturated NaHCO$_3$ solution (0.6 mL) was added and 30 min later, the mixture was diluted with CHCl$_3$ (1 mL) and water (0.4 mL). The organic layer was washed with water (0.4 mL) and the solvent was removed using a speedvac. The urea product was typically obtained as a solid in good yield (>90%) and with high purity (>95% by LC/MS). In some cases, the product was purified by flash chromatography, using EtOAc/hexanes as the eluent.

2.2 Results 1-(2-Cyclohexyl-4-oxo-4H-quinazolin-3-yl)-3-(2-fluorobenzyl)-urea $^1$H NMR (CDCl$_3$) δ 8.10 (d, J=8.0 Hz, 1H), 7.6-7.7 (m, 2H), 6.9-7.4 (m, 5H), 4.39 (d, J=33.7 Hz, 2H), 2.9-3.1 (m, 1H), 2.50 (t, J=7.5 Hz, 2H), 1.6-2.0 (m, 6H), 1.2-1.6 (m, 4H); MS(ESI): 395 (M+H)$^+$.

Example 3

3.1a General Preparative Method for Amide Quinazolines

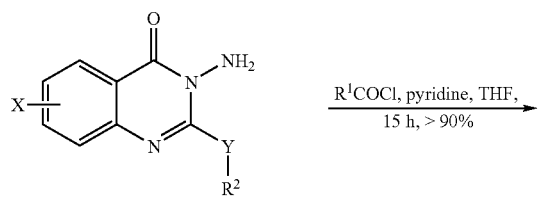

Scheme 13

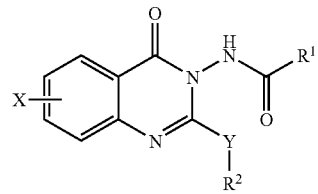

According to Scheme 13, the starting 3-aminoquinazolinone (0.1 mmol) was dissolved in dry THF (1 mL) and treated with pyridine (1.5 equivalents) followed by an acid chloride (1.2 equivalents). After 15 h, saturated NaHCO$_3$ solution (0.6 mL) was added and 30 min later, the mixture was diluted with EtOAc (2 mL) and water (0.4 mL). The organic layer was washed with water (0.4 mL). Removal of the solvent with a speedvac typically provided the amide product as a solid in good yield (>90%) and with high purity (>95% by LC/MS). In some cases, the product was purified by flash chromatography, using EtOAc/hexanes as the eluent.

3.1b Alternate General Preparative Method for Amide Fused Ring Heterocycles

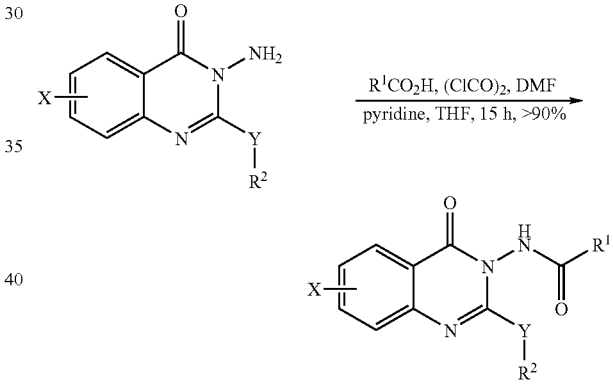

Scheme 14

Scheme 14 sets forth a method in which a carboxylic acid (1.2 equivalents) was dissolved in dry THF (1 mL) and treated with dry DMF (1 drop) followed by oxalyl chloride (1.3 equivalents; gas evolution; mild exotherm). After 1 h, pyridine (1 equivalent) was added (immediate precipitate), followed by the 3-aminoquinazolinone (0.1 mmol) and then more pyridine (2 equivalents). After 15 h, saturated NaHCO$_3$ solution (0.6 mL) was added and 30 min later, the mixture was diluted with EtOAc (2 mL) and water (0.4 mL). The organic layer was washed with water (0.4 mL). Removal of the solvent with a speedvac typically provided the amide product as a solid in good yield (>90%) and with high purity (>95% by LC/MS). In some cases, the product was purified by flash chromatography, using EtOAc/hexanes as the eluent.

3.1c General Procedure for Preparing Isatoic Anhydrides

As set forth in Scheme 6, anhydrous pyridine (2 eq) was added to a solution of anthranilic acid (1 eq) in dry methylene chloride and acetonitrile (1:1, 40 mL/g of 2-aminobenzoic acid) at room temperature. Solid triphosgene (⅓ eq) was then added in one portion and the resulting mixture was heated at 50° C. for 2 h. The resulting solid was collected by filtration and dried in vacuo. The crude isatoic anhydrides (VIII) were typically obtained in 50-80% yields. Though contaminated with some pyridinium hydrochloride, the anhydrides were used in the next step without further purification.

3.1d General Procedure for Preparing Acylhydrazides

A mixture of isatoic anhydride (1 eq) and appropriate phenylacetyl hydrazide (1.1 eq) were heated in glacial AcOH (4 ml/mmol) at 50° C. for 2-6 h. The resulting solution was cooled and water was added while shaking. The white precipitate was collected by filtration, washed with water and dried in vacuo at 50° C. for 4 h. The desired products were obtained as white solids in high purity (typically >90%) and moderate yields (typically 45-60%).

3.1e General Procedure for Preparing Nitro-benzoic-N'-phenylacetyl hydrazides The appropriate nitro-benzoic acid derivative (1 eq) was stirred in dry methylene chloride (100 mL/g of acid) at room temperature and to this was added two drops of N,N-dimethylformamide (DMF). Neat oxalyl chloride (2 eq) was then added to the mixture drop-wise at such a rate as to control gas evolution. After stirring for 2 h, the volatiles are removed by rotary evaporation and the remaining material was re-dissolved in dry methylene chloride (100 mL/g of acid). Pyridine (2 eq) and the appropriate hydrazide derivative (1 eq) were added consecutively and the mixture was allowed to stir at room temperature until the reaction is judged to be complete by HPLC analysis whereupon the reaction mixture was poured into water. The organic layer was removed and the water layer was extracted three times with ethyl acetate. The combined organic layers were dried ($Na_2SO_4$) and concentrated to provide the desired nitro-benzoic-N'-phenylacetyl hydrazides in high purity (typically >95%) and yields ranging from 40 to 90%.

3.1f General Procedure for Preparing 2-Amino-benzoic Acid N'-phenylacetyl-hydrazides from Nitro-benzoic-N'-phenylacetyl hydrazides Hydrogen (1 Atm) was applied to a mixture of nitro-benzoic-N'-phenylacetyl hydrazide in methanol (100 mL/g of hydrazide) and 10% palladium on activated carbon (100 mg/g of hydrazide). The reaction mixture was stirred at rt for 1-10 h. The resulting mixture was filtered through Celite/silica gel and concentrated under reduced pressure. The desired 2-amino-benzoic acid N'-phenylacetyl hydrazides were, in general, used directly in the next step without any further purification. In those instances when the desired products were contaminated, the hydrazides were purified by silica gel chromatography using EtOA/chexanes.

3.2 Results

N-(2-Cyclohexyl-4-oxo-4H-quinazolin-3-yl)-3,3-dimethyl-butyramide $^1$H NMR (CDCl$_3$) δ 8.19 (d, J=8.0 Hz, 1H), 7.6-7.8 (m, 2H), 7.4-7.5 (m, 1H), 2.8-2.9 (m, 1H), 2.36 (s, 3H), 1.2-2.0 (m, 10H), 1.14 (s, 9H); MS(ESI): 342 (M+H)$^+$.

N-(2-Cyclohexyl-4-oxo-4H-quinazolin-3-yl)-3-cyclopentyl-propionamide $^1$H NMR (CDCl$_3$) δ 8.18 (dd, J=1.0, 8.0 Hz, 1H), 7.6-7.8 (m, 2H), 7.3-7.5 (m, 1H), 2.7-2.9 (m, 1H), 2.50 (t, J=7.5 Hz, 2H), 1.2-2.0 (m, 21H); MS(ESI): 368 (M+H)$^+$.

N-(2-Isopropyl-4-oxo-4H-quinazolin-3-yl)-2-(3-trifluoromethoxyphenyl)-acetamide $^1$H NMR (CDCl$_3$) δ 8.18 (d, J=8.0 Hz, 1H), 7.6-7.8 (m, 2H), 7.1-7.5 (m, 5H), 3.8-4.0 (m, 2H), 3.00 (h, J=6.8 Hz, 1H), 1.25 (d, J=6.7 Hz, 3H), 1.18 (d, J=6.8 Hz, 3H); MS(ESI): 406 (M+H)$^+$.

1-(2-Cyclohexyl-4-oxo-4H-quinazolin-3-yl)-3-(2-fluorobenzyl)-urea $^1$H NMR (CDCl$_3$) δ 8.10 (d, J=8.0 Hz, 1H), 7.6-7.7 (m, 2H), 6.9-7.4 (m, 5H), 4.39 (d, J=33.7 Hz, 2H), 2.9-3.1 (m, 1H), 2.50 (t, J=7.5 Hz, 2H), 1.6-2.0 (m, 6H), 1.2-1.6 (m, 4H); MS(ESI): 395 (M+H)$^+$.

N-(2-Ethyl-7-fluoro-4-oxo-4H-quinazolin-3-yl)-2-(4-fluorophenyl)-acetamide $^1$H NMR (CDCl$_3$) δ 8.19 (dd, J=6.1, 8.7 Hz, 1H), 7.0-7.4 (m, 6H), 3.7-3.9 (m, 2H), 2.67 (q, J=7.3 Hz, 2H), 1.25 (t, J=7.3 Hz, 3H); MS(ESI): 344 (M+H)$^+$.

N-(7-Fluoro-4-oxo-(2-tetrahydrofuran-3-yl)-4H-quinazolin-3-yl)-2-(4-fluorophenyl)-acetamide $^1$H NMR (CDCl$_3$) δ 8.1-8.2 (m, 1H), 7.0-7.5 (m, 6H), 3.7-4.1 (m, 6H), 3.4-3.6 (m, 1H), 2.0-2.3 (m, 2H); MS(ESI): 386 (M+H)$^+$.

N-(2-Cyclopropyl-4-oxo-7-trifluoromethyl-4H-quinazolin-3-yl)-2-phenyl-acetamide $^1$H NMR (CDCl$_3$) δ 8.23 (d, J=8.4 Hz, 1H), 7.82 (s, 1H), 7.54 (d, J=8.5 Hz, 1H), 7.3-7.5 (m, 5H), 3.8-4.0 (m, 2H), 2.0-2.1 (m, 1H), 1.2-1.3 (m, 2H), 0.9-1.0 (m, 2H); MS(ESI): 388 (M+H)$^+$.

N-(2-Ethyl-4-oxo-7-trifluoromethoxy-4H-quinazolin-3-yl)-2-phenyl-acetamide $^1$H NMR (CDCl$_3$) δ 8.21 (d, J=8.8 Hz, 1H), 7.50 (s, 1H), 7.2-7.4 (m, 6H), 3.8-4.0 (m, 2H), 2.68 (q, J=7.3 Hz, 2H), 1.25 (t, J=7.4 Hz, 3H); MS(ESI): 392 (M+H)$^+$.

N-(2-Methyl-4-oxo-8-trifluoromethyl-4H-quinazolin-3-yl)-2-phenyl-acetamide $^1$H NMR (CDCl$_3$) δ 8.36 (d, J=7.9 Hz, 1H), 8.05 (d, J=7.7 Hz, 1H), 7.3-7.5 (m, 6H), 3.8-4.0 (m, 2H), 2.47 (s, 3H); MS(ESI): 362 (M+H)$^+$.

N-(2-Ethyl-4-oxo-8-trifluoromethyl-4H-quinazolin-3-yl)-2-phenyl-acetamide $^1$H NMR (CDCl$_3$) δ 8.36 (d, J=8.0 Hz, 1H), 8.05 (d, J=7.5 Hz, 1H), 7.3-7.5 (m, 6H), 3.8-4.0 (m, 2H), 2.69 (q, J=7.3 Hz, 2H), 1.28 (t, J=7.3 Hz, 3H); MS(ESI): 376 (M+H)$^+$.

N-(2-Cloproyl-4-oxo-8-trifluoromethyl-4H-quinazolin-3-yl)-2-(3,4-difluorophenyl)-acetamide $^1$H NMR (CDCl$_3$) δ 8.33 (d, J=7.3 Hz, 1H), 8.01 (d, J=7.4 Hz, 1H), 7.43 (t, J=7.8, Hz, 1H), 7.1-7.3 (m, 3H), 3.83 (s, 2H), 2.0-2.1 (m, 1H), 1.3-1.4 (m, 2H), 1.0-1.1 (m, 2H); MS(ESI): 424 (M+H)$^+$.

N-(2-Cloproyl-4-oxo-8-trifluoromethyl-4H-quinazolin-3-yl)-3-(3-fluorophenyl)-propionamide $^1$H NMR (CDCl$_3$) δ 8.32 (d, J=8.0 Hz, 1H), 8.00 (d, J=7.5 Hz, 1H), 7.41 (t, J=7.6, Hz, 1H), 7.2-7.3 (m, 1H), 6.8-7.1 (m, 3H), 3.8-3.2 (m, 2H), 2.7-2.9 (m, 2H), 1.8-1.9 (m, 1H), 1.2-1.4 (m, 2H), 0.9-1.1 (m, 2H); MS(ESI): 420 (M+H)$^+$.

N-(2-Ethyl-4-oxo-8-trifluoromethoxy-4H-quinazolin-3-yl)-2-phenyl-acetamide $^1$H NMR (CDCl$_3$) δ 8.13 (dd, J=1.4, 8.0 Hz, 1H), 7.64 (d, J=8.0 Hz, 1H), 7.3-7.5 (m, 6H), 3.8-4.0 (m, 2H), 2.70 (q, J=7.3 Hz, 2H), 1.27 (t, J=7.3 Hz, 3H); MS(ESI): 392 (M+H)$^+$.

2-(3-Fluorophenyl)-N-(4-oxo-2-propyl-8-trifluoromethoxy-4H-quinazolin-3-yl)-acetamide $^1$H NMR (CDCl$_3$) δ 8.14 (dd, J=1.4, 8.1 Hz, 1H), 7.65 (d, J=8.0 Hz, 1H), 7.3-7.5 (m, 2H), 7.0-7.2 (m, 3H), 3.8-4.0 (m, 2H), 2.63 (t, J=7.5 Hz, 2H), 1.7-1.9 (m, 2H), 0.96 (t, J=7.5 Hz, 3H); MS(ESI): 424 (M+H)$^+$.

N-(2-(1,1-Difluoroethyl)-4-oxo-8-trifluoromethyl-4H-quinazolin-3-yl)-2-phenyl-acetamide $^1$H NMR (CDCl$_3$) δ 8.40 (d, J=7.8 Hz, 1H), 8.07 (d, J=7.7 Hz, 1H), 7.60 (dd, J=7.7, 7.7 Hz, 1H), 7.2-7.4 (m, 5H), 3.76 (s, 2H), 2.03 (t, J=19.1 Hz, 3H); MS(ESI): 412 (M+H)$^+$.

N-(8-Chloro-2-(1,1-difluoroethyl)-4-oxo-4H-quinazolin-3-yl)-2-(4-fluorophenyl)-acetamide $^1$H NMR (CDCl$_3$) δ 8.11 (dd, J=2.5, 8.0 Hz, 1H), 7.84 (dd, J=2.2, 7.6 Hz, 1H), 7.44 (ddd, J=3.7, 8.0, 8.0 Hz, 1H), 7.2-7.4 (m, 2H), 6.99 (m, 2H), 3.71 (d, J=3.3 Hz, 2H), 2.06 (dt, J=3.5, 19.1 Hz, 3H); MS(ESI): 396 (M+H)$^+$.

Example 4

4.1 General Procedure for Preparing Substituted Fused Ring Heterocycles

Acid chloride (1 eq) was added to a solution of 2-aminobenzoic acid N'-phenylacetyl hydrazide (1 eq) and pyridine (1 eq) in anhydrous dioxane (5 mL/1 mmol) at rt. The mixture was heated at 50° C. for 1 h (or until LCMS indicated that the acylation complete). 4N HCl in dioxane (0.1 ml/1 mmol) was added and the solution heated at 60-70° C. for 2-6 h. The solvent was removed under reduced pressure and the desired substituted fused ring heterocycles were purified by column chromatography (EtOAc/hexanes). The compounds were obtained as off-white solids in high purity (>95% LC) and moderate to high yields (55-95%).

4.2 Results

N-(2-tert-Butyl-7-fluoro-4-oxo-4H-quinazolin-3-yl)-2-(4-fluorophenyl)-acetamide $^1$H NMR (CDCl$_3$) δ 8.14 (dd, J=6.3, 8.9 Hz, 1H), 7.70 (brs, 1H), 7.40 (dd, J=5.2, 8.3 Hz, 2H), 7.32 (dd, J=2.1, 9.8 Hz, 1H), 7.18-7.07 (m, 3H), 3.91-3.77 (m, 2H), 1.32 (s, 9H); MS(ESI): 372 (M+H)$^+$.

N-(2-Ethyl-8-methyl-4-oxo-4H-quinazolin-3-yl)-2-(4-fluorophenyl)-acetamide $^1$H NMR (CDCl$_3$) δ 8.66 (brs, 1H), 7.99 (d, J=7.8 Hz, 1H), 7.58 (d, J=7.8 Hz, 1H), 7.38-7.30 (m, 3H), 7.03 (t, J=8.6 Hz, 2H), 3.86-3.72 (m, 2H), 2.72-2.60 (m, 2H), 2.58 (s, 3H), 1.26 (t, J=7.3, 3H); MS(ESI): 340 (M+H)$^+$.

N-(8-Chloro-2-ethyl-4-oxo-4H-quinazolin-3-yl)-2-phenyl-acetamide $^1$H NMR (CDCl$_3$) δ 8.70 (brs, 1H), 8.03 (dd, J=1.2, 8.0 Hz, 1H), 7.81 (dd, J1.2, 8.0 Hz, 1H), 7.38-7.30 (m, 3H), 7.12-6.98 (m, 3H), 3.83-3.70-(m, 2H), 2.78-2.67 (q, J=7.3 Hz, 2H), 1.26 (t, J=7.3, 3H); MS(ESI): 361 (M+H)$^+$.

Example 5

5.1 General Procedure for Preparing 1,1-Dioxo-1H-1λ$^6$-benzo[1,2,4]thiadiazin-2-yl Derivatives Substituted 2-nitro-sulfonyl chloride was added drop-wise to a stirring solution of hydrazide and pyridine in THF at rt. After 1 h the solvent was removed and the residue was purified by passage through a short silica plug (EtOAc/hexane; 1:2). The concentrated product was dissolved in anhydrous methanol (5-mil/mmol) and anhydrous Na$_2$SO$_4$ was added (~200 mg/mmol). 10% Pd/C was added (10% w/w) and 1 atm of hydrogen was applied. The mixture was stirred for 4 h after which the mixture was filtered through a mixture of silica/celite (1:1 EtOAc/hexanes). Concentration of the eluent gave the crude anilines as solids in high purity (>95% LCMS) and high yield (80-90%). Treatment of the anilines with the appropriate orthoester in an anhydrous acidic medium at elevated temperatures (60-100° C.) gave the desired cyclized products. Purification by column chromatography afforded the products as off-white solids in high yield (>80%) and purity (>95%).

5.2 Results

N-(3-Ethyl-1,1-dioxo-1H-1λ$^6$-benzo[1,2,4]thiadiazin-2-yl)-2-phenyl-acetamide $^1$H NMR (CDCl$_3$) δ 8.31 (brs, 1H), 7.83 (d, J=7.8 Hz, 1H), 7.68-7.66 (m, 2H), 7.48-7.35 (m, 6H), 3.78 (s, 2H), 2.55 (q, J=7.3 Hz, 2H), 1.18 (t, J=7.3 Hz, 3H); MS(ESI): 344 (M+H)$^+$.

Example 6

6.1 General Procedure for Preparing 5-Membered Fused Ring Heterocycles

Scheme 15

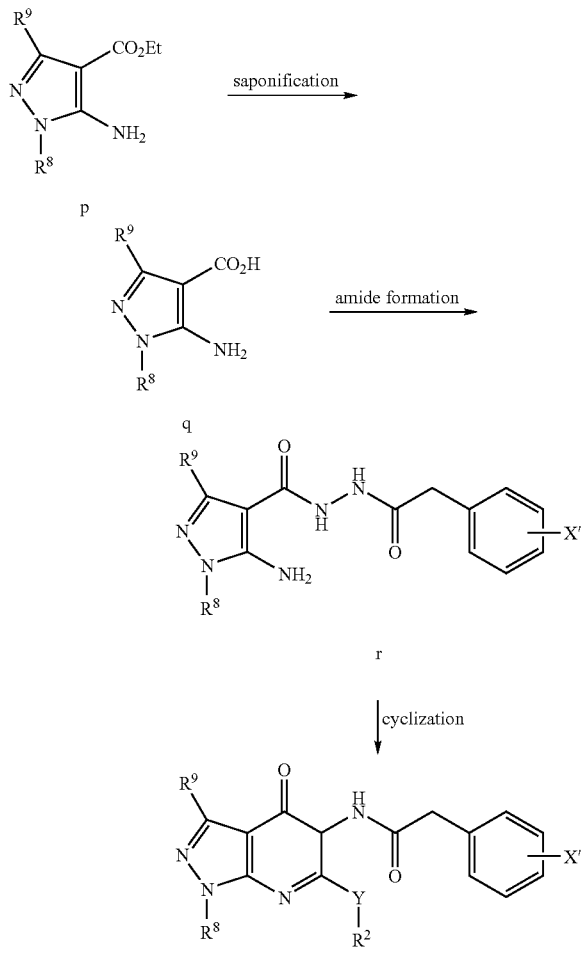

Ethyl ester p (0.003 mol) was added to a solution of KOH (1.1 eq, 0.0033 mol) in water (4 ml) at room temperature. The resulting mixture was heated at 100 oC (sealed vial) while stirring. After 15 min the reaction was checked by LCMS. If starting material remained a further 0.1 eq of KOH was added and heating continued for 20 min. Reaction was cooled to 0 oC whereupon 6N HCl (aq) was added until pH~3 was attained. The resulting white solid q was collected by filtration and dried in vacuo (50 oC) for 3 h. Yields were typically 40-70% with purities typically >95%.

BOP (1 eq) was added to a suspension of acid q (1 eq), hydrazide (1.5 eq) and Et3N (3 eq) in EtOAc/THF (2:1, 6 ml per mmol). The resulting suspension was shaken at room temperature overnight. Solvent was removed and EtOAc (6 ml/mmol) was added. The mixture was warmed until a clear solution formed. Washed with water (2×3 ml), saturated NaHCO3 (aq) (2×3 ml), saturated NH4Cl (2×3 ml) then water again (3 ml). Hexane (6 ml) was added to the organic layer. Precipitate was collected by filtration and dried in vacuo. If no precipitate formed the reaction was concentrated and purified by column chromatography (Hexanes/EtOAc). Products were afforded as white solid in yields 60-85% with purities >95%.

Alternative methods were used to form the 5-membered fused ring heterocycle s using either orthoester or acid chloride. In the former, the corresponding orthoester (0.2 ml) and a catalytic amount of pTSA (~5 mg) was added to a solution of r (0.1 mmol) in dioxane (0.5 ml) was added. The solution was heated at 80 oC until conversion was complete (typically 3-8 h). Solvent was removed under reduced pressure and the products were purified by column chromatography (Hexanes/EtOAc). Products were afforded as white solids in yields 60-90% with purities >95%.

Alternatively, the desired carbonyl chloride (1.3 eq) and pyridine (1 eq) was added to a solution of r (0.1 mmol) in dioxane (0.5 ml). The reaction was stirred and heated at 55 oC for 3 h. 0.5 ml of 1N HCl in ether (or 0.1 ml of 4N HCl in dioxane) was added and the reaction heated at 100° C. until complete. Solvent was removed under reduced pressure and the products were purified by column chromatography (Hexanes/EtOAc). Products were afforded as white solids in yields 20-70% with purities >95%.

6.2 Results

5-Amino-1-(2,2,2-trifluoro-ethyl)-1H-pyrazole-4-carboxylic acid N'-phenylacetyl-hydrazide $^1$H NMR (d6-DMSO) δ 9.92 (brs, 1H), 9.62 (brs, 1H), 7.76 (s, 1H), 7.31-7.21 (m, 5H), 6.59 (brs, 2H), 4.88 (q, J=9.1 Hz, 2H), 3.47 (s, 2H); $^{19}$F NMR (d6-DMSO) 6-69.2 (t, J=8.6 Hz, 3F); MS(ESI): 342 (M+H)$^+$.

5-Amino-1-(2,2,2-trifluoro-ethyl)-1H-pyrazole-4-carboxylic acid N'-[2-(4-fluoro-phenyl)-acetyl]-hydrazide $^1$H NMR (d$_6$-DMSO) δ 9.91 (brs, 1H), 9.62 (brs, 1H), 7.76 (s, 1H), 7.36-7.31 (dd, J=8.4 & 5.9 Hz, 2H), 7.15-7.09 (t, J=8.8 Hz, 2H), 6.58 (brs, 2H), 4.87 (q, J=9.1 Hz, 2H), 3.47 (s, 2H); MS(ESI): 360 (M+H)$^+$.

N-[6-Ethyl-4-oxo-1-(2,2,2-trifluoro-ethyl)-1,4-dihydro-pyrazolo[3,4-d]pyrimidin-5-yl]-2-phenyl-acetamide $^1$H NMR (d$_6$-DMSO) δ 11.2 (s, 1H), 8.25 (s, 1H), 7.35-7.23 (m, 5H), 5.22 (q, J=8.8 Hz, 2H), 3.74 (m, 2H), 3.07-2.44 (m, 2H); $^{19}$F NMR (d$_6$-DMSO) δ −69.2 (t, J=8.6 Hz, 3F); MS(ESI): 380 (M+H)$^+$.

N-[6-Methyl-4-oxo-1-(2,2,2-trifluoro-ethyl)-1,4-dihydro-pyrazolo[3,4-d]pyrimidin-5-yl]-2-phenyl-acetamide $^1$H NMR (d$_6$-DMSO) δ 11.2 (s, 1H), 8.24 (s, 1H), 7.37-7.25 (m, 5H), 5.21 (q, J=9.0 Hz, 2H), 3.72 (m, 2H), 2.31 (s, 3H); $^{19}$F NMR (d$_6$-DMSO) δ −69.2 (t, J=8.5 Hz, 3F); MS(ESI): 366 (M+H)$^+$.

Example 7

This example illustrates a screening protocol for evaluating putative potassium channel agonists for the ability to open voltage-gated potassium channels.

7.1 Materials and Methods

NG108-15 cells, a mouse neuroblastoma, rat glioma hybrid cell line, functionally express M-currents (Robbins et al., *J. Physiol.* 451: 159-85 (1992). NG108-15 M-currents are likely comprised, at least in part, of KCNQ2, KCNQ3 and KCNQ5, since these genes are reportedly robustly expressed in differentiated NG108-15 cells (Selyanko et al., *J. Neurosci.* 19(18): 7742-56 (1999); Schroeder et al., *J. Biol. Chem.* 275 (31): 24089-95 (2000)) and KCNQ3 dominant-negative constructs reduce M-current density in these cells (Selyanko et al., *J. Neurosci.* 22(5): RC212 (2002).

NG108-15 were maintained in DMEM (high glucose) supplemented with 10% fetal bovine serum, 0.05 mM pyridoxine, 0.1 mM hypoxanthine, 400 nM aminopterin, 16 mM thymidine, 50 μgml$^{-1}$ gentamycin and 10 mM HEPES, in an incubator at 37° C. with a humidified atmosphere of 5% $CO_2$. Cells were plated in 96 well plates differentiated by addition of 10 μM PGE1 and 50 μM isomethylbutylxanthine to the growth media prior to study.

Differentiated NG108-15 cells were loaded with voltage-sensitive dye by incubation in Earls Balanced Salt Solution (EBSS) containing 5 mM DiBAC for 1 h. Following loading, drug solution containing 5 mM DiBAC was added to each well. Changes in fluorescence were measured every 30 s for 25 min. The maximum change in fluorescence was measured and expressed as a percentage of the maximum response obtained in the presence of a positive control agent.

7.2 Results

Table 1 sets forth potencies of representative compounds of the invention in the NG-108-15 FLIPR assay, for a selection of compounds.

TABLE 1

| Compound ID # | Activity |
|---|---|
| 1 | +++ |
| 10 | + |
| 18 | +++ |
| 20 | +++ |
| 22 | +++ |
| 29 | ++ |
| 33 | +++ |
| 35 | + |
| 43 | ++ |
| 50 | +++ |
| 51 | +++ |
| 57 | +++ |
| 62 | ++ |
| 63 | +++ |
| 65 | +++ |
| 66 | + |
| 69 | +++ |
| 72 | + |
| 89 | +++ |
| 91 | +++ |
| 95 | +++ |
| 100 | + |
| 110 | +++ |
| 134 | +++ |
| 159 | ++ |
| 166 | ++ |
| 169 | +++ |
| 180 | +++ |
| 196 | ++ |
| 199 | + |
| 205 | ++ |
| 206 | +++ |
| 215 | +++ |
| 217 | ++ |
| 233 | ++ |
| 242 | +++ |
| 244 | +++ |
| 247 | ++ |
| 271 | +++ |

TABLE 1-continued

| Compound ID # | Activity |
|---|---|
| 273 | +++ |
| 278 | +++ |
| 293 | + |
| 301 | +++ |
| 310 | ++ |
| 314 | +++ |
| 320 | +++ |
| 331 | ++ |
| 348 | +++ |
| 354 | +++ |
| 358 | +++ |
| 359 | +++ |
| 360 | +++ |
| 364 | +++ |
| 365 | +++ |
| 366 | +++ |
| 384 | ++ |
| 385 | +++ |
| 391 | ++ |
| 392 | ++ |
| 393 | + |
| 416 | + |
| 421 | + |
| 420 | ++ |

+ Represents 10 μM < $EC_{50}$ < 3 μM;
++ represents 3 μM < $EC_{50}$ < 0.5 μM;
+++ represents $EC_{50}$ < 0.5 μM.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of the formula:

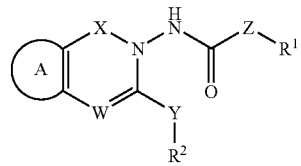

in which
A is a member selected from the group consisting of substituted phenyl, substituted or unsubstituted imidazolyl, substituted or unsubstituted thiazolyl, substituted or unsubstituted oxazolyl, substituted or unsubstituted triazolyl, substituted or unsubstituted isothiazolyl, substituted or unsubstituted isoxazolyl, substituted or unsubstituted 1,2,3,-oxadiazolyl, and six-membered substituted or unsubstituted heteroaryl, substituted or unsubstituted $C_4$-$C_8$ cycloalkyl, and substituted or unsubstituted 5-8 membered heterocyclyl;

X is a member selected from CO and CS;

W is N;

Z is a member selected from the group consisting of —$CH_2$—, —CHF—, —$CF_2$—, and —$NR^4(CR^{4a}R^{4b})_s$— wherein $R^4$ is a member selected from H and a substituted or unsubstituted $C_1$-$C_5$ alkyl group;

$R^{4a}$ and $R^{4b}$ are members independently selected from H, substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl;

s is an integer from 1 to 3;

Y is $(CR^5R^6)_n$, wherein n is an integer from 0-4; and $R^5$ and $R^6$ are members independently selected from H, F, substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl;

$R^1$ is a member selected from substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl; and $R^2$ is a member selected from the group consisting of $CF_3$, substituted or unsubstituted $C_1$-$C_8$ alkyl selected from methyl, ethyl, n-propyl, isopropyl, n-butyl, t-butyl, isobutyl, sec-butyl, cyclohexyl, (cyclohexyl)methyl, cyclopropylmethyl, and homologs and isomers of n-pentyl, n-hexyl, n-heptyl, n-octyl; substituted or unsubstituted aryl, substituted or unsubstituted heteroaryl, substituted or unsubstituted $C_3$-$C_8$ cycloalkyl, substituted or unsubstituted 3-7-membered heterocyclyl, such that when X is C(O), A is a substituted phenyl forming a 1,3-benzodioxolyl ring; and Y—$R^2$ is unsubstituted acyclic alkyl, acyclic alkyl substituted with an amide or unsubstituted phenyl, then Z-$R^1$ is other than acyclic alkyl substituted with unsubstituted phenyl, and acyclic alkyl substituted with 4-phenyl-1-halo.

2. A compound according to claim 1 in which A is a member from the group consisting of substituted or unsubstituted imidazolyl, substituted or unsubstituted thiazolyl, substituted or unsubstituted oxazolyl, substituted or unsubstituted triazolyl, substituted or unsubstituted isothiazolyl, substituted or unsubstituted isoxazolyl, substituted or unsubstituted 1,2,3,-oxadiazolyl, and substituted or unsubstituted 6-membered heteroaryl.

3. A compound according to claim 2 in which A is substituted or unsubstituted 6-membered heteroaryl.

4. A compound according to claim 2 in which A is substituted by one or two groups selected from halogen.

5. A compound according to claim 1 in which A is substituted phenyl.

6. A compound according to claim 5 in which A is phenyl substituted by one or two groups selected from halogen, nitrile, substituted or unsubstituted $C_1$-$C_4$ alkyl, $SCF_3$, trifluoromethyl and trifluoromethoxy.

7. A compound according to claim 1 in which X is CO.

8. A compound according to claim 1 in which Z is —$CH_2$—.

9. A compound according to claim 1 in which $R^1$ is a member selected from substituted or unsubstituted aryl, and substituted or unsubstituted heteroaryl.

10. A compound according to claim 1 in which $R^1$ is substituted or unsubstituted phenyl.

11. A compound according to claim 10 in which $R^1$ is a member selected from phenyl, and phenyl substituted with one or more of halogen, $CF_3$ and $OCF_3$.

12. A compound according to claim 1 in which $R^2$ is an unbustituted $C_1$-$C_6$ acyclic alkyl group selected from $CF_3$, methyl, ethyl, n-propyl, isopropyl, n-butyl, t-butyl, isobutyl, sec-butyl, and the acylic homologs and isomers of n-pentyl and n-hexyl.

13. A compound according to claim 12 in which Y is —$CF_2$— or n is 0.

14. A compound according to claim 12 in which $R^2$ is methyl, ethyl, n-propyl, isopropyl, n-butyl, t-butyl, isobutyl, sec-butyl or $CF_3$.

15. A compound according to claim 14 in which Y is —$CF_2$— or n is 0.

16. A compound according to claim 1 in which A is a member selected from substituted or unsubstituted imidazolyl, substituted or unsubstituted thiazolyl, substituted or unsubstituted oxazolyl, substituted or unsubstituted triazolyl, substituted or unsubstituted isothiazolyl, substituted or unsubstituted isoxazolyl, and substituted or unsubstituted 1,2,3,-oxadiazolyl.

17. A compound according to claim 16 wherein A is substituted with $R^8$ and $R^9$, wherein $R^8$ and $R^9$ are independently selected from:

H, halo, $CF_3$, $CF_3O$, $NO_2$, CN, $S(O)_mR^{10}$, $COOR^{11}$, $CONR^{12}R^{13}$, $SO_2NR^{12}R^{13}$, $S(O)_mCF_3$, $CH_2CF_3$, substituted or unsubstituted $C_1$-$C_6$ alkyl, and substituted or unsubstituted $C_3$-$C_7$ cycloalkyl, wherein $R^{10}$ and $R^{11}$ are independently selected from substituted or unsubstituted $C_1$-$C_5$ alkyl, and substituted or unsubstituted $C_3$-$C_7$ cycloalkyl;

m is an integer from 0 to 2; and $R^{12}$ and $R^{13}$ are independently selected from H, substituted or unsubstituted $C_1$-$C_5$ alkyl, substituted or unsubstituted $C_3$-$C_7$ cycloalkyl, or $R^{12}$ and $R^{13}$, together with the nitrogen atom to which they are attached, form a 5- to 7-membered ring.

18. The compound according to claim 17 wherein A is substituted or unsubstituted imidazolyl.

19. The compound according to claim 18, wherein A is unsubstituted imidazolyl or $R^8$ and $R^9$ are independently selected from $CF_3$, unsubstituted $C_1$-$C_6$ alkyl, unsubstituted $C_3$-$C_7$ cycloalkyl, $OCF_3$ and $CH_2CF_3$.

20. The compound according to claim 18 wherein $R^8$ and $R^9$ are independently selected from $CF_3$, substituted or unsubstituted $C_1$-$C_6$ alkyl, substituted or unsubstituted $C_3$-$C_7$ cycloalkyl, $OCF_3$ and $CH_2CF_3$.

21. A compound according to claim 17 wherein

X is CO;

Z is $CH_2$; and $R^1$ is substituted or unsubstituted phenyl.

22. A compound according to claim 17 wherein $R^2$ is a member selected from substituted or unsubstituted $C_1$-$C_4$ alkyl, substituted or unsubstituted $C_3$-$C_6$ cycloalkyl and substituted or unsubstituted $C_3$-$C_6$ heterocyclyl; and $R^8$ and $R^9$ are members independently selected from H, halo, $CF_3$, $OCF_3$, substituted or unsubstituted $C_1$-$C_5$ alkyl, $SCF_3$, $CH_2CF_3$ and CN.

23. The compound according to claim 21 wherein Y is —$CF_2$— or n is 0.

24. A compound of the formula:

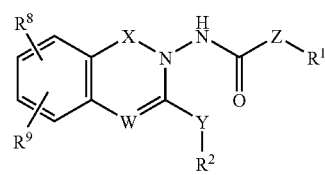

in which
X is a member selected from CO and CS;
W is N;
Z is a member selected from —CH$_2$—, —CHF—, —CF$_2$— and —NR$^4$(CR$^{4a}$R$^{4b}$)$_s$—
  wherein R$^4$ is a member selected from H and a substituted or unsubstituted C$_1$-C$_5$ alkyl group;
  R$^{4a}$ and R$^{4b}$ are members independently selected from H, substituted or unsubstituted aryl, substituted or unsubstituted heteroaryl, substituted or unsubstituted C$_3$-C$_8$ cycloalkyl, substituted or unsubstituted 5-7 membered heterocyclyl, and substituted or unsubstituted C$_1$-C$_8$ alkyl;
  s is an integer from 1 to 3;
Y is (CR$^5$R$^6$)$_n$, wherein n is an integer from 0-4; and R$^5$ and R$^6$ are members independently selected from H, F, substituted or unsubstituted aryl, substituted or unsubstituted heteroaryl, substituted or unsubstituted C$_3$-C$_8$ cycloalkyl, substituted or unsubstituted 5-7 membered heterocyclyl, and substituted or unsubstituted C$_1$-C$_8$ alkyl;
R$^1$ is a member selected from substituted or unsubstituted aryl, substituted or unsubstituted heteroaryl, substituted or unsubstituted C$_3$-C$_8$ cycloalkyl, substituted or unsubstituted 5-7 membered heterocyclyl, and substituted or unsubstituted C$_1$-C$_8$ alkyl;
R$^2$ is a member selected from CF$_3$, substituted or unsubstituted C$_1$-C$_8$ alkyl selected from methyl, ethyl, n-propyl, isopropyl, n-butyl, t-butyl, isobutyl, sec-butyl, cyclohexyl, (cyclohexyl)methyl, cyclopropylmethyl, and homologs and isomers of n-pentyl, n-hexyl, n-heptyl, n-oxtyl, substituted or unsubstituted aryl, substituted or unsubstituted heteroaryl, substituted or unsubstituted C$_3$-C$_8$ cycloalkyl, and substituted or unsubstituted 3-7 membered saturated heterocyclyl;
R$^8$ and R$^9$ are independently selected from H, halo, CF$_3$, CF$_3$O, NO$_2$, CN, S(O)$_m$R$^{10}$, COOR$^{11}$, CONR$^{12}$R$^{13}$, SO$_2$NR$^{12}$R$^{13}$, S(O)$_m$CF$_3$, substituted or unsubstituted C$_1$-C$_6$ alkyl, and substituted or unsubstituted C$_3$-C$_7$ cycloalkyl, with the proviso that R$^8$ and R$^9$ are not both H; or R$^8$ and R$^9$ are taken together with the atoms to which they are attached to form a dioxolyl ring;
  wherein R$^{10}$ and R$^{11}$ are independently selected from substituted or unsubstituted C$_1$-C$_5$ alkyl, and substituted or unsubstituted C$_3$-C$_7$ cycloalkyl;
  m is an integer from 0 to 2; and
  R$^{12}$ and R$^{13}$ are independently selected from H, substituted or unsubstituted C$_1$-C$_5$ alkyl, substituted or unsubstituted C$_3$-C$_7$ cycloalkyl, or R$^{12}$ and R$^{13}$, together with the nitrogen atom to which they are attached, form a 5- to 7-membered ring,
  such that when X is C(O), R$^8$ is halogen and R$^9$ is H or R$^8$ and R$^9$ taken together with the carbon atoms to which they are joined form a dioxolyl ring, and Y—R$^2$ is unsubstituted acyclic alkyl, acyclic alkyl substituted with an amide or unsubstituted phenyl, then Z-R$^1$ is other than acyclic alkyl substituted with unsubstituted phenyl, and acyclic alkyl substituted with 4-phenyl-1-halo.
25. The compound according to claim 24 wherein X is CO;
  Z is CH$_2$; and
  R$^1$ is substituted or unsubstituted phenyl.
26. The compound according to claim 24 wherein
  R$^2$ is a member selected from unsubstituted C$_1$-C$_4$ alkyl selected from methyl, ethyl, n-propyl, isopropyl, n-butyl, t-butyl, isobutyl, and sec-butyl, substituted or unsubstituted C$_3$-C$_6$ cycloalkyl and substituted or unsubstituted C$_3$-C$_6$ heterocyclyl; and
  R$^8$ and R$^9$ are members independently selected from halo, CF$_3$, OCF$_3$, substituted or unsubstituted C$_1$-C$_5$ alkyl, SCF$_3$, CH$_2$CF$_3$ and CN.
27. The compound according to claim 26 wherein Y is —CF$_2$— or n is 0.
28. A compound of the formula:

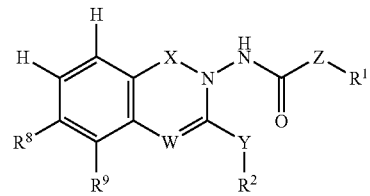

in which
X is a member selected from CO and CS;
W is N;
Z is a member selected from —CH$_2$—, —CHF—, —CF$_2$— and —NR$^4$(CR$^{4a}$R$^{4b}$)$_s$—
  wherein R$^4$ is a member selected from H and a substituted or unsubstituted C$_1$-C$_5$ alkyl group;
  R$^{4a}$ and R$^{4b}$ are members independently selected from H, substituted or unsubstituted aryl, substituted or unsubstituted heteroaryl, substituted or unsubstituted C$_3$-C$_8$ cycloalkyl, substituted or unsubstituted 5-7 membered heterocyclyl, and substituted or unsubstituted C$_1$-C$_8$ alkyl;
  s is an integer from 1 to 3;
R$^1$ is a member selected from substituted or unsubstituted aryl, substituted or unsubstituted heteroaryl, substituted or unsubstituted C$_3$-C$_8$ cycloalkyl, substituted or unsubstituted 5-7 membered heterocyclyl, substituted or unsubstituted C$_1$-C$_8$ alkyl;
Y is (CR$^5$R$^6$)$_n$, wherein n is an integer from 0-4; and R$^5$ and R$^6$ are members independently selected from H, F, substituted or unsubstituted aryl, substituted or unsubstituted heteroaryl, substituted or unsubstituted C$_3$-C$_8$ cycloalkyl, substituted or unsubstituted 5-7 membered heterocyclyl, and substituted or unsubstituted C$_1$-C$_8$ alkyl;
R$^2$ is a member selected from CF$_3$, substituted or unsubstituted C$_1$-C$_8$ alkyl, selected from methyl, ethyl, n-propyl, isopropyl, n-butyl, isobutyl, sec-butyl, cyclohexyl, (cyclohexyl)methyl, cyclopropylmethyl, and homologs and isomers of n-pentyl, n-hexyl, n-heptyl, n-octyl, substituted or unsubstituted aryl, substituted or unsubstituted heteroaryl, substituted or unsubstituted C$_3$-C$_8$ cycloalkyl, substituted or unsubstituted 3-7 membered saturated heterocyclyl;
R$^8$ and R$^9$ are independently selected from H, halo, CF$_3$O, NO$_2$, CN, S(O)$_m$R$^{10}$, COOR$^{11}$, CONR$^{12}$R$^{13}$, SO$_2$NR$^{12}$R$^{13}$, substituted or unsubstituted C$_1$-C$_6$ alkyl, and substituted or unsubstituted C$_3$-C$_7$ cycloalkyl, with the proviso that R$^8$ and R$^9$ are not both H;
  wherein R$^{10}$ is a member selected from CF$_3$ and substituted or unsubstituted C$_1$-C$_5$ alkyl, and substituted or unsubstituted C$_3$-C$_7$ cycloalkyl; and R$^{11}$ is a member selected from substituted or unsubstituted C$_1$-C$_5$ alkyl, and substituted or unsubstituted C$_3$-C$_7$ cycloalkyl;
  m is an integer from 0 to 2; and
  R$^{12}$ and R$^{13}$ are independently selected from H, substituted or unsubstituted C$_1$-C$_5$ alkyl, substituted or unsubstituted $C_3$-$C_7$ cycloalkyl, or $R^{12}$ and $R^{13}$, taken together with the nitrogen atom to which they are attached, form a 5- to 7-membered ring.

29. The compound according to claim 28 wherein
X is CO;
Z is $CH_2$; and
$R^1$ is substituted or unsubstituted phenyl.

30. The compound according to claim 27 wherein
$R^1$ is a member selected from phenyl and phenyl substituted with one or more of halogen, $CF_3$ and $OCF_3$;
$R^2$ is a member selected from unsubstituted $C_1$-$C_4$ alkyl selected from methyl, ethyl, n-propyl, isopropyl, n-butyl, t-butyl, isobutyl, sec-butyl, unsubstituted $C_3$-$C_6$ cycloalkyl and unsubstituted $C_3$-$C_7$ heterocyclyl; and
$R^8$ and $R^9$ are members independently selected from H, halo, $CF_3$, $OCF_3$, unsubstituted $C_1$-$C_5$ alkyl, $CH_2CF_3$, $SCF_3$ and CN, with the proviso that $R^8$ and $R^9$ are not both H.

31. The compound according to claim 30 wherein Y is —$CF_2$— or n is 0.

32. The compound according to claim 30 wherein $R^8$ is H; $R^9$ is $CF_3$; n is 0; $R^2$ is $C_1$-$C_4$ alkyl; and $R^1$ is phenyl substituted with a halo.

33. A composition comprising a pharmaceutically acceptable excipient and an effective amount of a compound according to claim 1.

34. A composition comprising a pharmaceutically acceptable excipient and a compound of the formula:

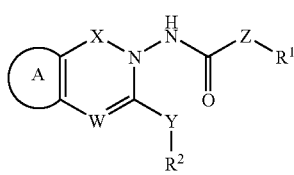

in which
A is a member selected from substituted phenyl; substituted or unsubstituted imidazolyl, substituted or unsubstituted thiazolyl, substituted or unsubstituted oxazolyl, substituted or unsubstituted triazolyl, substituted or unsubstituted isothiazolyl, substituted or unsubstituted isoxazolyl, substituted or unsubstituted 1,2,3,-oxadiazolyl, and six-membered substituted or unsubstituted heteroaryl, substituted or unsubstituted $C_4$-$C_8$ cycloalkyl, and substituted or unsubstituted 5-8 membered heterocyclyl;
X is a member selected from CO and CS;
W is N;
Z is a member selected from the group consisting of —$CH_2$—, —CHF—, —$CF_2$—, and —$NR^4(CR^{4a}R^{4b})_s$—
wherein $R^4$ is a member selected from H and a substituted or unsubstituted $C_1$-$C_5$ alkyl group;
$R^{4a}$ and $R^{4b}$ are members independently selected from H, substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl;
s is an integer from 1 to 3;
Y is $(CR^5R^6)_n$, wherein n is an integer from 0-4; and $R^5$ and $R^6$ are members independently selected from H, F, substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl;
$R^1$ is a member selected from substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl; and
$R^2$ is a member selected from the group consisting of $CF_3$, substituted or unsubstituted $C_1$-$C_8$ alkyl selected from methyl, ethyl, n-propyl, isopropyl, n-butyl, t-butyl, isobutyl, sec-butyl, cyclohexyl, (chclohexyl)methyl, cyclopropylmethyl, and homologs and isomers of n-pentyl, n-hexyl, n-heptyl, n-octyl, substituted or unsubstituted aryl, substituted or unsubstituted heteroaryl, substituted or unsubstituted $C_3$-$C_8$ cycloalkyl, substituted or unsubstituted 3-7-membered heterocyclyl,
such that when X is C(O), A is a substituted phenyl forming a 1,3-benzodioxolyl ring; and Y—$R^2$ is unsubstituted acyclic alkyl, acyclic alkyl substituted with an amide or unsubstituted phenyl, then Z-$R^1$ is other than acyclic alkyl substituted with unsubstituted phenyl, and acyclic alkyl substituted with 4-phenyl-1-halo.

35. A composition comprising a pharmaceutically acceptable excipient and a compound of the formula:

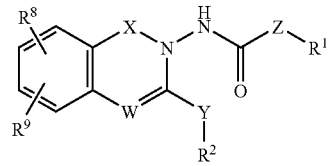

in which
X is a member selected from CO and CS;
W is N;
Z is a member selected from —$CH_2$—, —CHF—, —$CF_2$— and —$NR^4(CR^{4a}R^{4b})_s$—
wherein $R^4$ is a member selected from H and a substituted or unsubstituted $C_1$-$C_5$ alkyl group;
$R^{4a}$ and $R^{4b}$ are members independently selected from H, substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl;
s is an integer from 1 to 3;
Y is $(CR^5R^6)_n$, wherein n is an integer from 0-4; and $R^5$ and $R^6$ are members independently selected from H, F, substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl;
$R^1$ is a member selected from substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl;
$R^2$ is a member selected from $CF_3$, substituted or unsubstituted $C_1$-$C_8$ alkyl selected from methyl, ethyl, n-propyl, isopropyl, n-butyl, t-butyl, isobutyl, sec-butyl, cyclohexyl, (cyclohexyl)methyl, cyclopropylmethyl, and homologs and isomers of n-pentyl, n-hexyl, n-heptyl, n-octyl, substituted or unsubstituted aryl, substituted or unsubstituted heteroaryl, substituted or unsubstituted $C_3$-$C_8$ cycloalkyl, substituted or unsubstituted 3-7 membered saturated heterocyclyl;

$R^8$ and $R^9$ are independently selected from H, halo, $CF_3$, $CF_3O$, $NO_2$, CN, $S(O)_m R^{10}$, $COOR^{11}$, $CONR^{12}R^{13}$, $SO_2NR^{12}R^{13}$, $S(O)_m CF_3$, substituted or unsubstituted $C_1$-$C_6$ alkyl, and substituted or unsubstituted $C_3$-$C_7$ cycloalkyl, with the proviso that $R^8$ and $R^9$ are not both H; or $R^8$ and $R^9$ are taken together with the atoms to which they are attached to form a dioxolyl ring;

wherein $R^{10}$ and $R^{11}$ are independently selected from substituted or unsubstituted $C_1$-$C_5$ alkyl, and substituted or unsubstituted $C_3$-$C_7$ cycloalkyl;

m is an integer from 0 to 2; and $R^{12}$ and $R^{13}$ are independently selected from H, substituted or unsubstituted $C_1$-$C_5$ alkyl, substituted or unsubstituted $C_3$-$C_7$ cycloalkyl, or $R^{12}$ and $R^{13}$, together with the nitrogen atom to which they are attached, form a 5- to 7-membered ring, such that when X is C(O), $R^8$ is halogen and $R^9$ is H or $R^8$ and $R^9$ taken together with the carbon atoms to which they are joined form a dioxolyl ring, and Y—$R^2$ is unsubstituted acyclic alkyl, acyclic alkyl substituted with an amide or unsubstituted phenyl, then Z- $R^1$ is other than acyclic alkyl substituted with unsubstituted phenyl, and acyclic alkyl substituted with 4-phenyl-1-halo.

36. A composition comprising a pharmaceutically acceptable excipient and a compound of the formula:

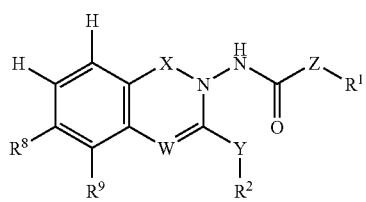

in which

X is a member selected from CO and CS;

W is N;

Z is a member selected from —$CH_2$—, —CHF—, —$CF_2$— and —$NR^4(CR^{4a}R^{4b})_s$— wherein $R^4$ is a member selected from H and a substituted or unsubstituted $C_1$-$C_5$ alkyl group;

$R^{4a}$ and $R^{4b}$ are members independently selected from H, substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl;

s is an integer from 1 to 3;

$R^1$ is a member selected from substituted or unsubstituted aryl, substituted or unsubstituted heteroaryl, substituted or unsubstituted $C_3$-$C_8$ cycloalkyl, substituted or unsubstituted 5-7 membered heterocyclyl, substituted or unsubstituted $C_1$-$C_8$ alkyl;

Y is $(CR^5R^6)_n$, wherein n is an integer from 0-4; and $R^5$ and $R^6$ are members independently selected from H, F, substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl;

$R^2$ is a member selected from $CF_3$, substituted or unsubstituted $C_1$-$C_8$ alkyl selected from methyl, ethyl, n-propyl, isopropyl, n-butyl, t-butyl, isobutyl, sec-butyl, cyclohexyl, (cyclohexyl)methyl, cyclopropylmethyl, and homologs and isomers of n-pentyl, n-hexyl, n-heptyl, n-octyl, substituted or unsubstituted aryl, substituted or unsubstituted heteroaryl, substituted or unsubstituted $C_3$-$C_8$ cycloalkyl, substituted or unsubstituted 3-7 membered saturated heterocyclyl;

$R^8$ and $R^9$ are independently selected from H, halo, $CF_3O$, $NO_2$, CN, $S(O)_m R^{10}$, $COOR^{11}$, $CONR^{12}R^{13}$, $SO_2NR^{12}R^{13}$, substituted or unsubstituted $C_1$-$C_6$ alkyl, and substituted or unsubstituted $C_3$-$C_7$ cycloalkyl, with the proviso that $R^8$ and $R^9$ are not both H;

wherein $R^{10}$ is a member selected from $CF_3$ and substituted or unsubstituted $C_1$-$C_5$ alkyl, and substituted or unsubstituted $C_3$-$C_7$ cycloalkyl; and $R^{11}$ is a member selected from substituted or unsubstituted $C_1$-$C_5$ alkyl, and substituted or unsubstituted $C_3$-$C_7$ cycloalkyl;

m is an integer from 0 to 2; and $R^{12}$ and $R^{13}$ are independently selected from H, substituted or unsubstituted $C_1$-$C_5$ alkyl, substituted or unsubstituted $C_3$-$C_7$ cycloalkyl, or $R^{12}$ and $R^{13}$, taken together with the nitrogen atom to which they are attached, form a 5- to 7-membered ring.

37. A compound of claim 1, wherein $R^2$ is substituted or unsubstituted $C_3$ to $C_8$ cycloalkyl.

38. A compound of claim 1, wherein X is CO, Z is —$CH_2$—, $R^1$ is a member selected from unsubstituted phenyl and phenyl substituted with one or more of halogen, $CF_3$ and $OCF_3$, and A is phenyl substituted with one or two groups selected from halogen; n is 0, and $R^2$ is unsubstituted $C_3$-$C_8$ cycloalkyl selected from the group consisting of cyclopropyl, cyclopentyl, cyclohexyl, and cycloheptyl.

39. A compound of claim 38, wherein A is phenyl substituted with one or more of halogen, and $R^2$ is unsubstituted cyclopropyl.

40. A compound of claim 1, wherein X is CO, Z is —$CH_2$—, $R^1$ is a member selected from unsubstituted phenyl and phenyl substituted with one or more of halogen, $CF_3$ and $OCF_3$, and A is phenyl substituted with one or two groups selected from halogen; n is 0; and $R^2$ is unsubstituted $C_1$-$C_8$ alkyl selected from methyl, ethyl, n-propyl, isopropyl, n-butyl, t-butyl, isobutyl, sec-butyl, (cyclohexyl)methyl, cyclopropylmethyl, and homologs and isomers of n-pentyl, n-hexyl, n-heptyl, n-octyl.

41. A composition comprising a pharmaceutically acceptable excipient and a compound of claim 38.

42. A composition comprising a pharmaceutically acceptable excipient and a compound of claim 39.

43. A compound of the formula:

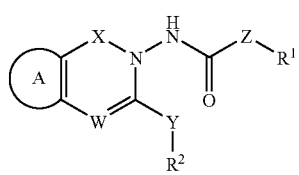

in which wherein A has the formula:

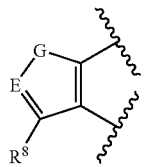

in which E is selected from $CR^9$ and N, and G is selected from O and S,

X is a member selected from CO and CS;

W is N;

Z is a member selected from the group consisting of —$CH_2$—, —CHF—, —$CF_2$—, and —$NR^4(CR^{4a}R^{4b})_s$— wherein $R^4$ is a member selected from H and a substituted or unsubstituted $C_1$-$C_5$ alkyl group;

$R^{4a}$ and $R^{4b}$ are members independently selected from H, substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl;

s is an integer from 1 to 3;

Y is $(CR^5R^6)_n$, wherein n is an integer from 0-4; and $R^5$ and $R^6$ are members independently selected from H, F, substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl;

$R^1$ is a member selected from substituted or unsubstituted aryl, substituted or unsubstituted heteroaryl, substituted or unsubstituted $C_3$-$C_8$ cycloalkyl, substituted or unsubstituted 5-7 membered heterocyclyl, and substituted or unsubstituted $C_1$-$C_8$ alkyl; and $R^2$ is a member selected from the group consisting of $CF_3$, substituted or unsubstituted $C_1$-$C_8$ alkyl selected from methyl, ethyl, n-propyl, isopropyl, n-butyl, t-butyl, isobutyl, sec-butyl, cyclohexyl, (cyclohexyl)methyl, cyclopropylmethyl, and homologs and isomers of n-pentyl, n-hexyl, n-heptyl, n-octyl; substituted or unsubstituted aryl, substituted or unsubstituted heteroaryl, substituted or unsubstituted $C_3$-$C_8$ cycloalkyl, and substituted or unsubstituted 3-7-membered heterocyclyl, $R^8$ and $R^9$ are independently selected from:

H, halo, $CF_3$, $CF_3O$, $NO_2$, CN, $S(O)_mR^{10}$, $COOR^{11}$, $CONR^{12}R^{13}$, $SO_2NR^{12}R^{13}$, $S(O)_mCF_3$, $CH_2CF_3$, substituted or unsubstituted $C_1$-$C_6$ alkyl, and substituted or unsubstituted $C_3$-$C_7$ cycloalkyl, wherein $R^{10}$ and $R^{11}$ are independently selected from substituted or unsubstituted $C_1$-$C_5$ alkyl, and substituted or unsubstituted $C_3$-$C_7$ cycloalkyl;

m is an integer from 0 to 2; and $R^{12}$ and $R^{13}$ are independently selected from H, substituted or unsubstituted $C_1$-$C_5$ alkyl, substituted or unsubstituted $C_3$-$C_7$ cycloalkyl, or $R^{12}$ and $R^{13}$, together with the nitrogen atom to which they are attached, form a 5- to 7-membered ring.

44. The compound according to claim 43 wherein $R^8$ and $R^9$ are independently selected from $CF_3$, substituted or unsubstituted $C_1$-$C_6$ alkyl, substituted or unsubstituted $C_3$-$C_7$ cycloalkyl, $OCF_3$, and $CH_2CF_3$.

45. A composition comprising a pharmaceutically acceptable excipient and a compound of claim 43.

* * * * *